US012569295B2

(12) United States Patent
    Tobey et al.

(10) Patent No.:  US 12,569,295 B2
(45) Date of Patent:  Mar. 10, 2026

(54) UNIPOLAR REFERENCE ELECTRODE FOR ELECTROPHYSIOLOGY MAPPING CATHETER

(71) Applicant: BIOSENSE WEBSTER (ISRAEL) LTD., Yokneam (IL)

(72) Inventors: Dustin R. Tobey, San Dimas, CA (US); Shubhayu Basu, Anaheim, CA (US); Cesar Fuentes-Ortega, Pasadena, CA (US); Pieter E. Van Niekerk, Monrovia, CA (US); Tushar Sharma, Arcadia, CA (US)

(73) Assignee: Biosense Webster (Israel) Ltd. Israel, Yokneam (IL)

( * ) Notice: Subject to any disclaimer, the term of this patent is extended or adjusted under 35 U.S.C. 154(b) by 1194 days.

(21) Appl. No.: 16/451,263

(22) Filed: Jun. 25, 2019

(65) Prior Publication Data

US 2020/0038101 A1      Feb. 6, 2020

Related U.S. Application Data

(60) Provisional application No. 62/714,110, filed on Aug. 3, 2018.

(51) Int. Cl.
    A61B 5/287          (2021.01)
    A61B 18/12          (2006.01)
    (Continued)

(52) U.S. Cl.
    CPC ...... A61B 18/1492 (2013.01); A61B 18/1206 (2013.01); A61B 5/287 (2021.01);
    (Continued)

(58) Field of Classification Search
    CPC ................ A61B 18/1492; A61B 5/287; A61B 2018/00351; A61B 5/6858;
    (Continued)

(56) References Cited

U.S. PATENT DOCUMENTS 5,398,683  A  *  3/1995  Edwards ................ A61B 5/287
                                                    607/116
5,738,096  A     4/1998  Ben-Haim
                (Continued)

FOREIGN PATENT DOCUMENTS

EP          2 641 556 A1      9/2013
EP            2139416 B1      8/2015
                (Continued)

OTHER PUBLICATIONS

European Search Report, Partial, and Provisional Written Opinion dated Dec. 5, 2019 for Application No. EP 19189827.9, 11 pgs.
(Continued)

*Primary Examiner* — Joseph A Stoklosa
*Assistant Examiner* — Brian M Antiskay
(74) *Attorney, Agent, or Firm* — FBT Gibbons LLP

(57)          ABSTRACT

An apparatus includes a shaft and an end effector at a distal end of the shaft. The end effector has a distal end and a proximal end with a longitudinal intermediate point between the distal and proximal ends. The end effector is sized to fit in an anatomical passageway within a cardiovascular system. The end effector includes at least one sensor electrode and a reference electrode. The at least one sensor electrode is configured to contact cardiovascular tissue and thereby pick up potentials. The reference electrode is configured to pick up a potential from fluid in contact with the reference electrode. The reference electrode is located proximal to the longitudinal intermediate point of the end effector. The end effector is configured to prevent the reference electrode from contacting tissue.

38 Claims, 14 Drawing Sheets

(51) Int. Cl.

| | |
|---|---|
| *A61B 18/14* | (2006.01) |
| *A61B 18/18* | (2006.01) |
| *A61B 5/00* | (2006.01) |
| *A61B 18/00* | (2006.01) |

(52) U.S. Cl.

CPC ... *A61B 5/6858* (2013.01); *A61B 2018/00351* (2013.01); *A61B 2018/00577* (2013.01); *A61B 2018/00839* (2013.01); *A61B 2018/1253* (2013.01); *A61B 2018/126* (2013.01)

(58) Field of Classification Search

CPC ........... A61B 2018/00839; A61B 2018/00267; A61B 5/053; A61B 2018/00214; A61B 2017/00243; A61B 2018/0016; A61B 2017/00026; A61B 5/0538; A61B 5/6859; A61B 2018/0212; A61B 2018/00363; A61B 2017/00053; A61B 5/061; A61B 2218/002; A61B 18/14; A61B 5/6852; A61B 2018/1475; A61B 2017/003; A61B 8/06; A61B 2017/00044

USPC ................ 600/372–374, 377, 380–381, 393, 600/434–435, 508–509; 606/20–42; 607/115–116, 119, 122–123

See application file for complete search history.

(56) References Cited

U.S. PATENT DOCUMENTS

| | | | |
|---|---|---|---|
| 5,782,239 | A | 7/1998 | Webster, Jr. |
| 5,797,903 | A | 8/1998 | Swanson et al. |
| 5,904,651 | A | 5/1999 | Swanson et al. |
| 6,014,579 | A | 1/2000 | Pomeranz et al. |
| 6,325,972 | B1 | 12/2001 | Jacobs et al. |
| 6,365,102 | B1 | 4/2002 | Wu et al. |
| 6,447,719 | B1 | 9/2002 | Agamohamadi et al. |
| 6,546,270 | B1 | 4/2003 | Goldin et al. |
| 6,852,277 | B2 | 2/2005 | Platt, Jr. et al. |
| 6,852,279 | B2 | 2/2005 | Williams et al. |
| 6,939,519 | B2 | 9/2005 | Agamohamadi et al. |
| 6,970,730 | B2 | 11/2005 | Fuimaono et al. |
| 8,346,339 | B2 | 1/2013 | Kordis et al. |
| 8,565,851 | B2 | 10/2013 | Lau et al. |
| 8,712,550 | B2 | 4/2014 | Grunewald |
| 8,956,353 | B2 | 2/2015 | Govari et al. |
| 9,031,642 | B2 | 5/2015 | Ghosh |
| 9,204,929 | B2 | 12/2015 | Solis |
| 9,480,416 | B2 | 11/2016 | Govari et al. |
| 9,801,585 | B2 | 10/2017 | Shah et al. |
| 9,820,664 | B2 | 11/2017 | Hoitink et al. |
| 9,833,161 | B2 | 12/2017 | Govari |
| 9,907,480 | B2 | 3/2018 | Basu et al. |
| 9,949,656 | B2 | 4/2018 | Wu et al. |
| 10,004,459 | B2 | 6/2018 | Werneth et al. |
| 10,111,623 | B2 | 10/2018 | Jung et al. |
| 10,595,738 | B2 | 3/2020 | Sterrett et al. |
| 10,987,045 | B2 | 4/2021 | Basu et al. |
| 11,648,043 | B2 | 5/2023 | Mihalik |
| 2002/0151807 | A1* | 10/2002 | Goldin .............. A61B 18/1492 600/509 |
| 2011/0028966 | A1* | 2/2011 | Lau .......................... A61N 1/06 606/41 |
| 2013/0030426 | A1 | 1/2013 | Gallardo et al. |
| 2013/0253504 | A1* | 9/2013 | Fang .................... A61B 5/4848 606/41 |
| 2015/0025526 | A1 | 1/2015 | Hua et al. |
| 2016/0143588 | A1* | 5/2016 | Hoitink ................ A61B 5/6859 600/374 |
| 2016/0228023 | A1 | 8/2016 | Govari |
| 2016/0374753 | A1 | 12/2016 | Wu et al. |
| 2017/0007157 | A1 | 1/2017 | Gross et al. |
| 2017/0007158 | A1* | 1/2017 | Gross ................... A61B 5/7475 |
| 2017/0252474 | A1 | 9/2017 | Thompson et al. |
| 2017/0296084 | A1* | 10/2017 | Blauer ................... A61B 5/287 |
| 2017/0312022 | A1 | 11/2017 | Beeckler et al. |
| 2018/0036078 | A1 | 2/2018 | Ditter |
| 2018/0056038 | A1 | 3/2018 | Aujla |
| 2018/0071017 | A1 | 3/2018 | Bar-Tal et al. |

FOREIGN PATENT DOCUMENTS

| | | |
|---|---|---|
| JP | 11-504541 A | 4/1999 |
| JP | 2011-152430 A | 8/2011 |
| JP | 2016-152926 A | 8/2016 |
| JP | 2018-47233 A | 3/2018 |
| WO | WO 2017/192480 A2 | 11/2017 |
| WO | WO 2019/156942 A1 | 8/2019 |

OTHER PUBLICATIONS

Translation of Japanese Notification of Reasons for Refusal for Application No. JP 2019-142872, dated Apr. 11, 2023, 4 pages.

Examination Report for Application No. EP 19189827.9, dated Apr. 19, 2023, 4 pages.

Extended European Search Report for Application No. EP 19189827. 9, dated Mar. 16, 2020, 11 pages.

Partial European Search Report for Application No. EP 19189827.9, dated Dec. 5, 2019, 12 pages.

Chinese First Office Action and Search Report dated Nov. 25, 2024, for Application No. 201910711974.3, 12 pages.

Chinese Second Office Action and Search Report dated Mar. 5, 2025, for Application No. 201910711974.3, 9 pages.

Chinese First Office Action and Search Report dated May 28, 2025, for Application No. 202510631842.5, 7 pages.

European Extended Search Report and Written Opinion dated Oct. 31, 2024, for Application No. 24194074.1, 9 pages.

Japanese Final Office Action dated Jul. 25, 2023, for Application No. 2019-142872, 2 pages.

Chinese Search Report dated Apr. 3, 2025, for Application No. 201910711974.3, 2 pages.

* cited by examiner

UNIPOLAR REFERENCE ELECTRODE FOR ELECTROPHYSIOLOGY MAPPING CATHETER

PRIORITY

This application claims priority to U.S. Provisional Pat. App. No. 62/714,110, entitled "Unipolar Reference Electrode for Electrophysiology Mapping Catheter," filed Aug. 3, 2018, the disclosure of which is incorporated by reference herein.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad that is in contact with the patient.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein; U.S. Pub. No. 2017/0312022, entitled "Irrigated Balloon Catheter with Flexible Circuit Electrode Assembly," published Nov. 2, 2017, the disclosure of which is incorporated by reference herein; U.S. Pub. No. 2018/0071017, entitled "Ablation Catheter with a Flexible Printed Circuit Board," published Mar. 15, 2018, the disclosure of which is incorporated by reference herein; U.S. Pub. No. 2018/0056038, entitled "Catheter with Bipole Electrode Spacer and Related Methods," published Mar. 1, 2018, the disclosure of which is incorporated by reference herein; U.S. Pub. No. 2018/0036078, entitled "Catheter with Soft Distal Tip for Mapping and Ablating Tubular Region," published Feb. 8, 2018, the disclosure of which is incorporated by reference herein; U.S. Pat. No. 8,956,353, entitled "Electrode Irrigation Using Micro-Jets," issued Feb. 17, 2015, the disclosure of which is incorporated by reference herein; and U.S. Pat. No. 9,801,585, entitled "Electrocardiogram Noise Reduction," issued Oct. 31, 2017, the disclosure of which is incorporated by reference herein.

Some catheter ablation procedures may be performed using electrophysiology (EP) mapping. Such EP mapping may include the use of sensing electrodes on a catheter (e.g., the same catheter that is used to perform the ablation). Such sensing electrodes may monitor electrical signals within the cardiovascular system to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein. Examples of EP mapping catheters are described in U.S. Pat. No. 9,907,480, entitled "Catheter Spine Assembly with Closely-Spaced Bipole Microelectrodes," issued Mar. 6, 2018, the disclosure of which is incorporated by reference herein; U.S. Pub. No. 2018/0036078, entitled "Catheter with Soft Distal Tip for Mapping and Ablating Tubular Region," published Feb. 8, 2018, the disclosure of which is incorporated by reference herein; and U.S. Pub. No. 2018/0056038, entitled "Catheter with Bipole Electrode Spacer and Related Methods," published Mar. 1, 2018, the disclosure of which is incorporated by reference herein.

In addition to using EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO system by Biosense Webster, Inc. of Irvine, California. Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein; and various other references that are cited herein.

While several catheter systems and methods have been made and used, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

Figure 1:
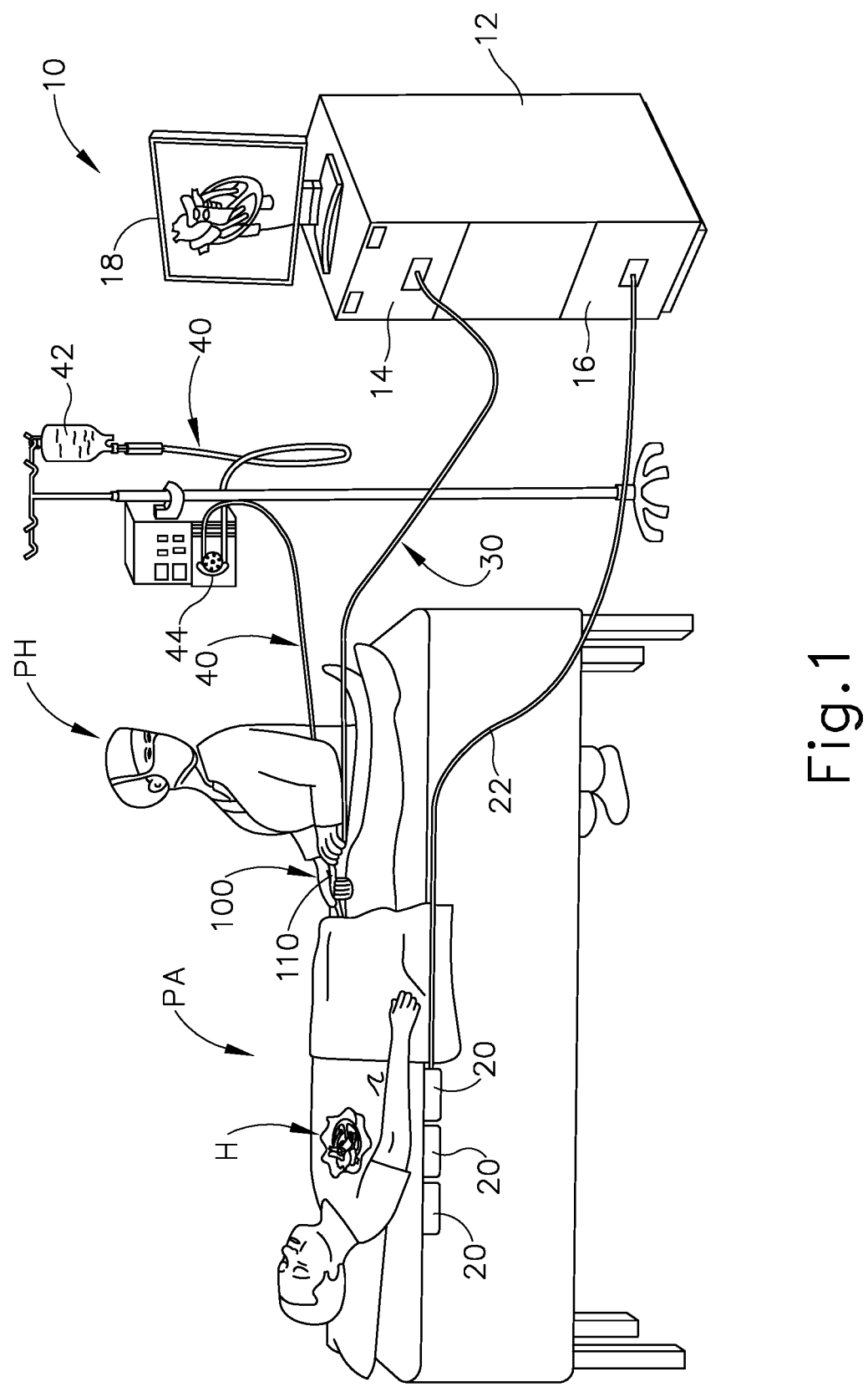
FIG. 1 depicts a schematic view of a medical procedure in which a catheter of a catheter assembly is inserted in a patient.

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. Exemplary Mapping Catheter System

A. Overview

Some EP mapping procedures may be performed using a unipolar electrode. Some conventional unipolar EP mapping techniques may include a comparison of a potential picked up by one unipolar electrode to a potential picked up by a remote reference electrode. An example of such a technique is the Wilson Central Terminal (WCT), which includes averaging three limb leads. Another technique may include the use of an electrode on a first catheter to pick up a potential at a tissue region of interest and an electrode on a second catheter to pick up a reference potential. For instance, an electrode on a first catheter may pick up a potential at tissue in a pulmonary vein (PV) while an electrode on a second catheter may pick up a reference potential in the inferior vena cava (IVC).

As an alternative to conventional unipolar EP mapping techniques, it may be desirable to obtain a reference potential from blood near the tissue at which a tissue potential is being picked up. In other words, it may be desirable to place a first electrode in contact with tissue to thereby pick up an electrical potential from the tissue; and place a second electrode in contact with blood near the contacted tissue to thereby pick up a reference electrical potential from the blood. The second (reference) electrode may only contact the blood without contacting tissue. The blood may provide an accurate reference potential of the heart. By having the second (reference) electrode avoid contact with tissue, the second (reference) electrode may avoid pickup up of local tissue potentials that might otherwise compromise the reliability of the sensed reference potential. This configuration may provide benefits similar to those obtained using bipolar EP mapping devices and techniques, such as reduced noise and reduced far field signals, due to the location of the reference electrode being in the same heart chamber as the tissue-contacting electrode; while still maintaining the features of a unipole signal, as a direct tissue potential is picked up by only one single electrode. By way of example only, this configuration may provide a reduction of far field signals of from approximately 50% to approximately 100% as compared to far field signals picked up using conventional techniques such as WCT.

Figure 2:
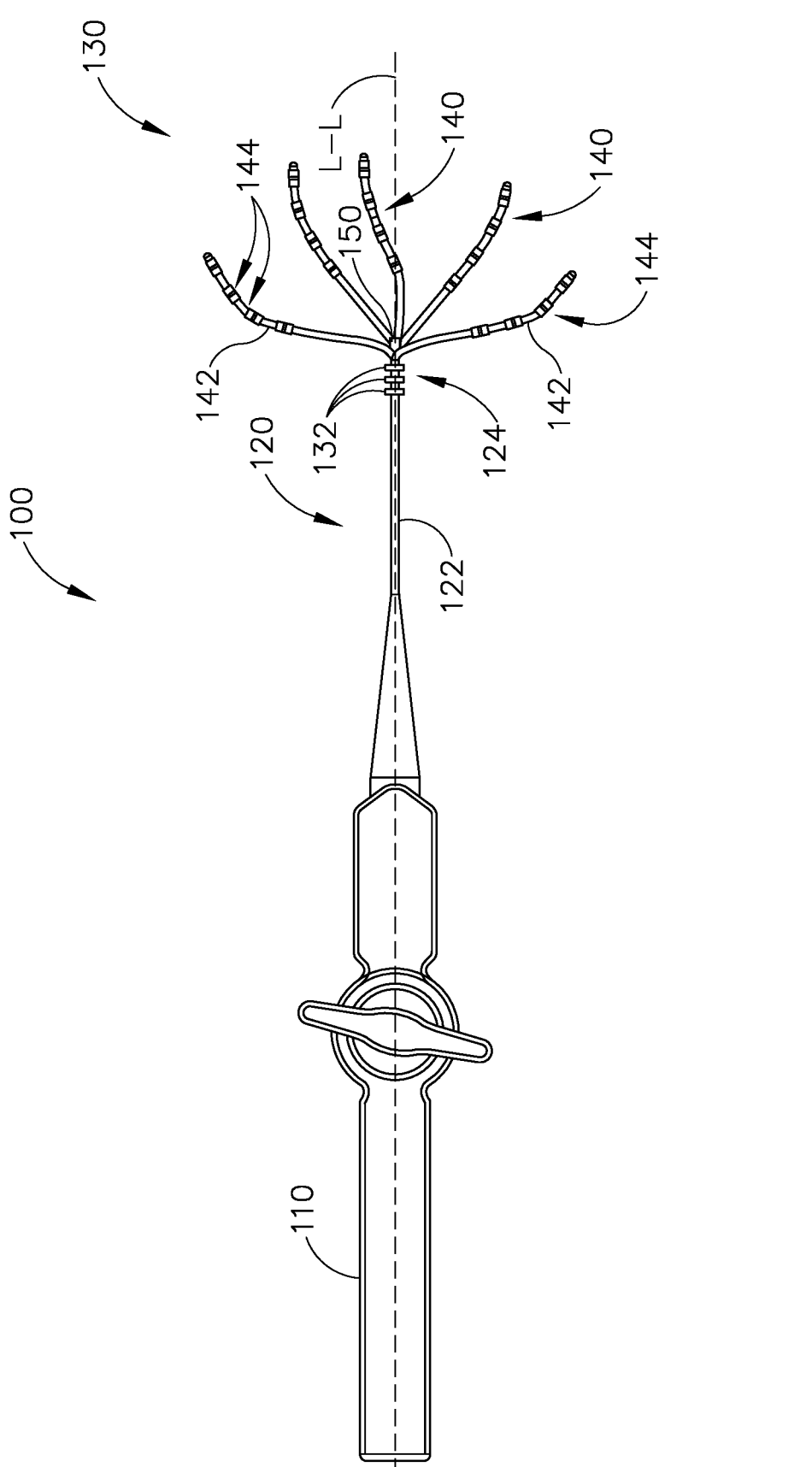
FIG. 2 depicts a top plan view of the catheter assembly of FIG. 1.

FIG. 1 shows an exemplary medical procedure and associated components of a cardiac EP mapping catheter system that may be used to provide non-conventional unipolar EP mapping as referred to above. In particular, FIG. 1 shows a physician (PH) grasping a handle (110) of a catheter assembly (100), with an end effector (130) of a catheter (120) (shown in FIGS. 2-4 but not shown in FIG. 1) of catheter assembly (100) disposed in a patient (PA) to perform EP mapping in or near the heart (H) of the patient (PA). As shown in FIG. 2, catheter (120) includes an elongate flexible shaft (122), with end effector (130) being disposed at a distal end (124) of shaft (122). End effector (130) and variations thereof will be described in greater detail below. Catheter assembly (100) is coupled with a guidance and drive system (10) via a cable (30). Catheter assembly (100) is also coupled with a fluid source (42) via a fluid conduit (40), though this is merely optional. A set of field generators (20) are positioned underneath the patient (PA) and are coupled with guidance and drive system (10) via another cable (22). Field generators (20) are also merely optional.

Guidance and drive system (10) of the present example includes a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via electrodes (132, 146, 148, 154) of end effector (130) as described in greater detail below. Console (12) includes a processor (not shown) that processes such EP mapping signals and thereby provides EP mapping as is known in the art. In addition, or in the alternative, first driver module (14) may be operable to provide RF power to electrodes (132, 146, 148) of end effector (130) to thereby ablate tissue. In some versions, first driver module (14) is also operable to receive position indicative signals from a position sensor (not shown) in end effector (130), as will be described in greater detail below. In such versions, the processor of console (12) is also operable to process the position indicative signals from the position sensor to thereby determine the position of the end effector (130) of catheter (120) within the patient (PA).

Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

As noted above, some versions of end effector (130) include a position sensor (not shown) that is operable to generate signals that are indicative of the position and orientation of end effector (130) within the patient (PA). Each position sensor may include a wire coil or a plurality of wire coils (e.g., three orthogonal coils) that are configured to generate electrical signals in response to the presence of an alternating electromagnetic field generated by field generators (20). Other components and techniques that may be used to generate real-time position data associated with end effector (130) may include wireless triangulation, acoustic tracking, optical tracking, inertial tracking, and the like. By way of example only, position sensing may be provided in accordance with at least some of the teachings of U.S. Pat. No. 9,480,416, the disclosure of which is incorporated by reference herein. Alternatively, end effector (130) may lack a position sensor.

Display (18) is coupled with the processor of console (12) and is operable to render images of patient anatomy. Such images may be based on a set of preoperatively or intraoperatively obtained images (e.g., a CT or MRI scan, 3-D map, etc.). The views of patient anatomy provided through display (18) may also change dynamically based on signals from the position sensor of end effector (130). For instance, as end effector (130) of catheter (120) moves within the patient (PA), the corresponding position data from the position sensor may cause the processor of console (12) to update the patient anatomy views in display (18) in real time to depict the regions of patient anatomy around end effector (130) as end effector (130) moves within the patient (PA). Moreover, the processor of console (12) may drive display (18) to show locations of aberrant conductive tissue sites, as detected via EP mapping with end effector (130). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (130) on the images of the patient's anatomy, such as by superimposing an illuminated dot, a crosshair, a graphical representation of end effector (130), or some other form of visual indication. Such a superimposed visual indication may also move within the images of the patient anatomy on display (18) in real time as the physician moves end effector (130) within the patient (PA), thereby providing real-time visual feedback to the operator about the position of end effector (130) within the patient (PA) as end effector (130) moves within the patient (PA). The images provided through display (18) may thus effectively provide a video tracking the position of end effector (130) within a patient (PA), without necessarily having any optical instrumentation (i.e., cameras) viewing end effector (130). In the same view, display (18) may simultaneously visually indicate the locations of aberrant conductive tissue sites detected through the EP mapping as described herein. The physician (PH) may thus view display (18) to observe the real time positioning of end effector (130) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). In some variations, conduit (40), fluid source (42), and pump (44) are omitted entirely. In versions where these components are included, end effector (130) may be configured to communicate irrigation fluid from fluid source (42) to the target site in the patient. Such irrigation may be provided in accordance with the teachings of any of the various patent references cited herein; or in any other suitable fashion as will be apparent to those skilled in the art in view of the teachings herein.

Figure 3:
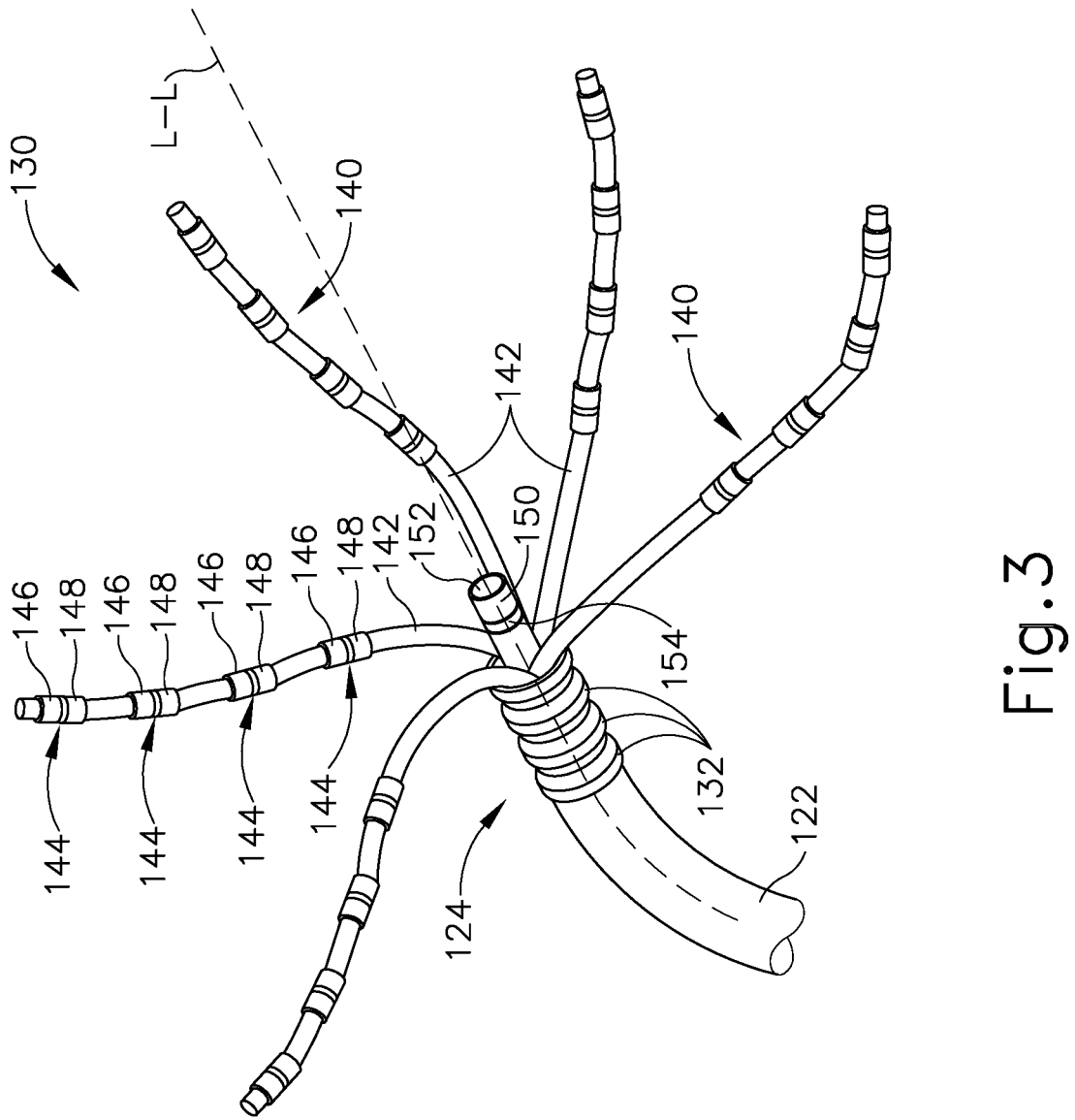
FIG. 3 depicts a perspective view of the end effector of the catheter assembly of FIG. 1.
Figure 4:
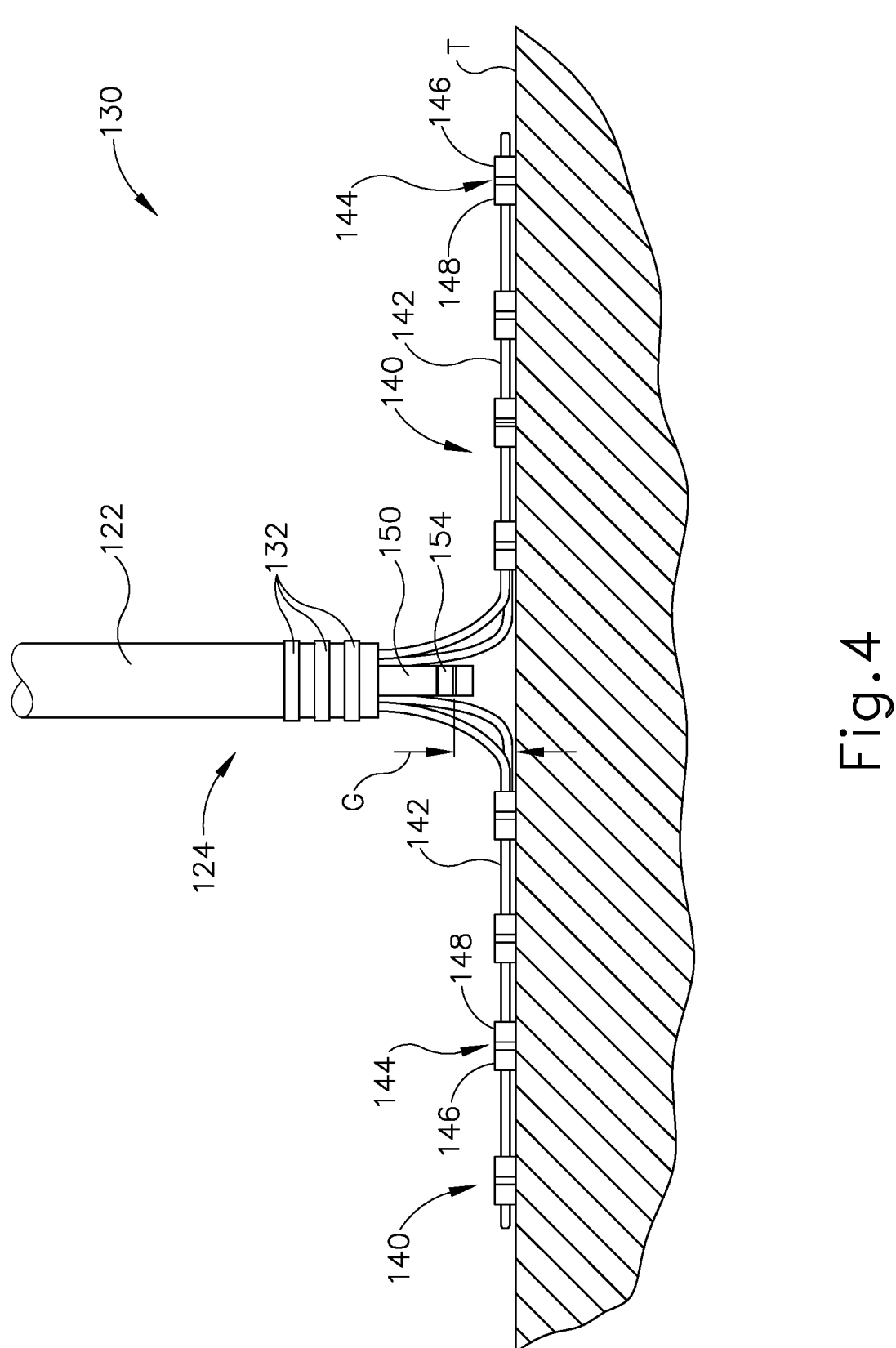
FIG. 4 depicts a side schematic view of the end effector of FIG. 3 contacting a tissue surface.

B. Exemplary Multi-Ray End Effector with Reference Electrode on Irrigation Shaft FIGS. 2-4 show end effector (130) in greater detail. In addition to the following, end effector (130) and other aspects of catheter assembly (100) may be configured and operable in accordance with at least some of the teachings of U.S. Pub. No. 2018/0056038, the disclosure of which is incorporated by reference herein. As shown, end effector (130) of the present example includes a set of spines or arms (140) extending distally from the distal end of catheter shaft (122). Arms (140) radiate generally outwardly away from the central longitudinal axis (L-L) of catheter shaft (122). In the present example, end effector (130) has five arms (140). In some other versions, end effector (130) has eight arms (140). Alternatively, end effector (130) may have any other suitable number of arms (140).

Each arm (140) includes a flexible elongate body (142) with a respective set of longitudinally spaced ring electrode (146, 148) pairs. Each arm (140) distally terminates in a respective free end. In the present example, each arm (140) has four pairs of electrodes (146, 148). Alternatively, more or fewer than four pairs of electrodes (146, 148) may be provided on each arm (140). The electrodes (146, 148) of each pair are separated from each other by a corresponding gap (144). In the present example, each pair of electrodes (146, 148) is configured to provide bipolar sensing of electrocardiogram signals as electrodes (146, 148) are placed in contact with cardiovascular tissue. Each pair of electrodes (146, 148) may also be used to provide unipolar sensing; or only a single electrode (146, 148) of each pair may be used to provide unipolar sensing while the other electrode (146, 148) of the pair is not used. Catheter assembly (100) may also enable the physician (PH) to toggle end effector (130) between two or more modes, including a bipolar sensing mode and a unipolar sensing mode. In some other variations, electrodes (146, 148) are not provided in pairs, such that each arm (140) only has either an array of electrodes (146) or an array of electrodes (148).

End effector (130) further includes a longitudinally spaced array of ring electrodes (132) at the distal end (124) of catheter shaft (122), proximal to arms (140). Electrodes (132) may also be configured to cooperate in pairs to provide bipolar sensing of electrocardiogram signals as electrodes (132) are placed in contact with cardiovascular tissue. Alternatively, one or more of electrodes (132) may be used to provide unipolar sensing. In some other versions, one or all of electrodes (132) are omitted.

End effector (130) further includes a central shaft (150) protruding distally from distal end (124) of catheter shaft (122), near the proximal ends of arms (140). Central shaft (150) is coaxially aligned with catheter shaft (122) and defines a distal opening (152), which is in communication with a lumen formed along the length of central shaft (150). This lumen is in fluid communication with fluid conduit (40), which is further in communication with fluid source (42) as described above. Central shaft (150) is thus operable to dispense irrigation fluid (e.g., saline) from fluid source (42) to a site within a patient (PA) (e.g., within a cardiovascular structure) via distal opening (152). In some other versions, central shaft (150) lacks distal opening (152) and is unable to otherwise dispense irrigation fluid.

Central shaft (150) of the present example further includes a ring electrode (154), which is configured to serve as a reference electrode as will be described in greater detail below. Ring electrode (154) is positioned to contact blood when end effector (130) is located within a cardiovascular structure in a patient (e.g., in the pulmonary vein, etc.). However, arms (140) are also configured to prevent ring electrode (154) from contacting tissue while end effector (130) is disposed in a cardiovascular structure. Thus, during normal use, one or more electrodes (146, 148) will contact tissue while ring electrode (154) does not contact tissue. For instance, as shown in FIG. 4, the physician (PH) may urge end effector (130) against a tissue surface (T). This may cause one or more arms (140) to generally flatten along the tissue surface (T), thereby placing electrodes (146, 148) in direct contact with the tissue surface (T). Ring electrode (154) may nevertheless be spaced away from the tissue surface (T) by a gap (G). Even if the physician were to continue urging end effector (130) further distally toward the tissue surface (T), and even if arms (140) were able to splay further outwardly, the distal end of central shaft (150) would contact the tissue surface (T) before ring electrode (154) would contact the tissue surface (T). Thus, during normal use of end effector (130), ring electrode (154) will not contact the tissue surface (T).

While ring electrode (154) does not contact the tissue surface (T), ring electrode (154) will nevertheless contact blood flowing through the cardiovascular system. If end effector (130) is positioned in the pulmonary vein, for example, one or more electrodes (146, 148) may contact the tissue surface (T) while ring electrode (154) contacts blood flowing through the pulmonary vein. The one or more electrodes (146, 148) contacting the tissue surface (T) may pick up electrical potentials at the contacted regions of the tissue surface (T), while ring electrode (154) picks up a reference potential from the blood in which ring electrode (154) is disposed. The processor of console (12) may process the potentials from electrodes (146, 148, 154) and thereby provide an electrocardiogram signal. Such electrocardiogram signals may be used to provide EP mapping to thereby identify locations of aberrant electrical activity within the cardiac anatomy. This may in turn allow the physician (PH) to identify the most appropriate regions of cardiac tissue to ablate (e.g., with RF energy, cryoablation, etc.), to thereby prevent or at least reduce the communication of aberrant electrical activity across the cardiac tissue.

Figure 5:
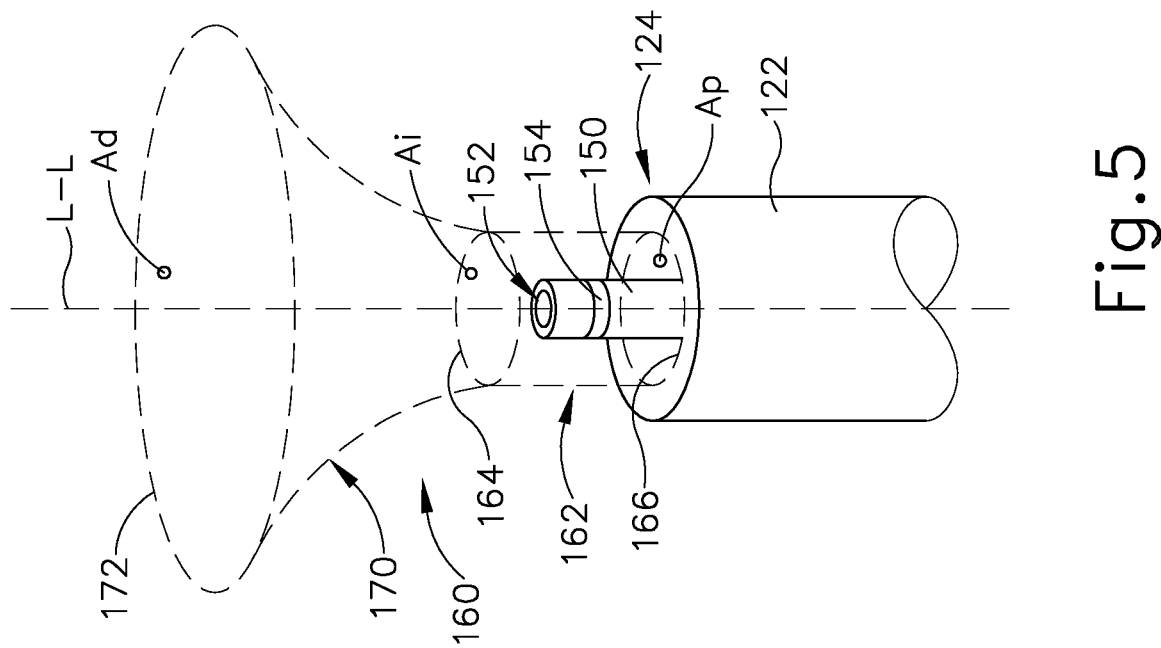
FIG. 5 depicts a perspective view of the end the distal end of the catheter assembly of FIG. 1, with end effector arms omitted, and with a schematic representation of an end effector profile including a cylindrical portion and a bell-mouth-shaped frusto-conical portion.

FIG. 5 shows an exemplary three-dimensional profile (160) that may be defined by at least proximal portions of arms (140). While arms (140) are omitted from FIG. 5, it should be understood that at least the proximal portions of arms (140) may be generally arranged around the boundary depicted as three-dimensional profile (160). In some versions, arms (140) are resiliently biased such that at least the proximal portions of arms (140) define three-dimensional profile (160). Three-dimensional profile (160) of this example includes a cylindrical portion (162) and a bell-mouth-shaped frusto-conical portion (170). Cylindrical portion (162) is proximally bounded by a proximal plane (166) and distally bounded by an intermediate plane (164). Proximal plane (166) is located at distal end (124) of catheter shaft (122). Bellmouth-shaped frusto-conical portion (170) is proximally bounded by intermediate plane (164) and distally bounded by distal plane (172).

In some versions, distal plane (172) is located at the free ends or distal tips of arms (140), such that arms (140) distally terminate at distal plane (172). In some other versions, arms (140) continue to extend distally along respective straight paths at distal plane (172), such that bellmouth-shaped frusto-conical portion (170) represents an intermediate curved portion of each arm (140) that is longitudinally interposed between respective distal and proximal straight portions of each arm (140). In some versions where arms (140) extend distally along respective straight paths at distal plane (172), these respective straight paths are obliquely oriented away from the longitudinal axis (L-L) of catheter shaft (122). An example of such a configuration is shown in FIG. 7, which depicts just one arm (140) of end effector (130), it being understood that the other arms (140) may be similarly configured (albeit arranged in an angularly spaced array).

Figure 6:
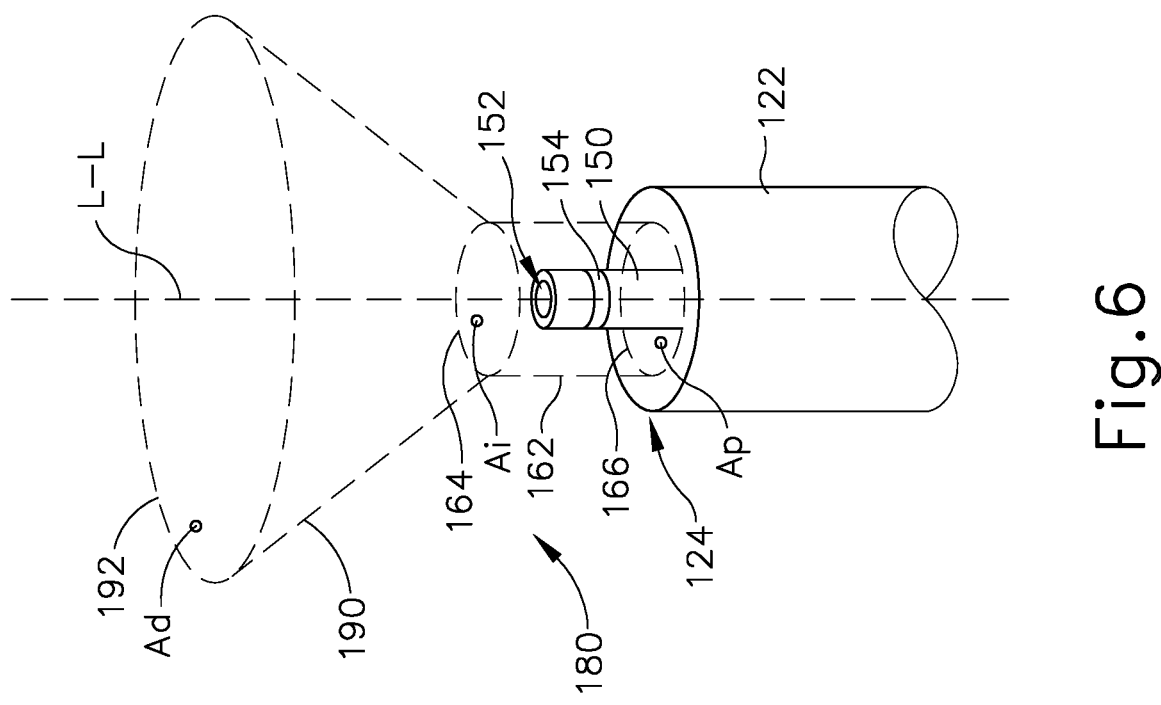
FIG. 6 depicts a perspective view of the end the distal end of the catheter assembly of FIG. 1, with end effector arms omitted, and with a schematic representation of an end effector profile including a cylindrical portion and a pyramid-shaped frusto-conical portion.
Figure 7:
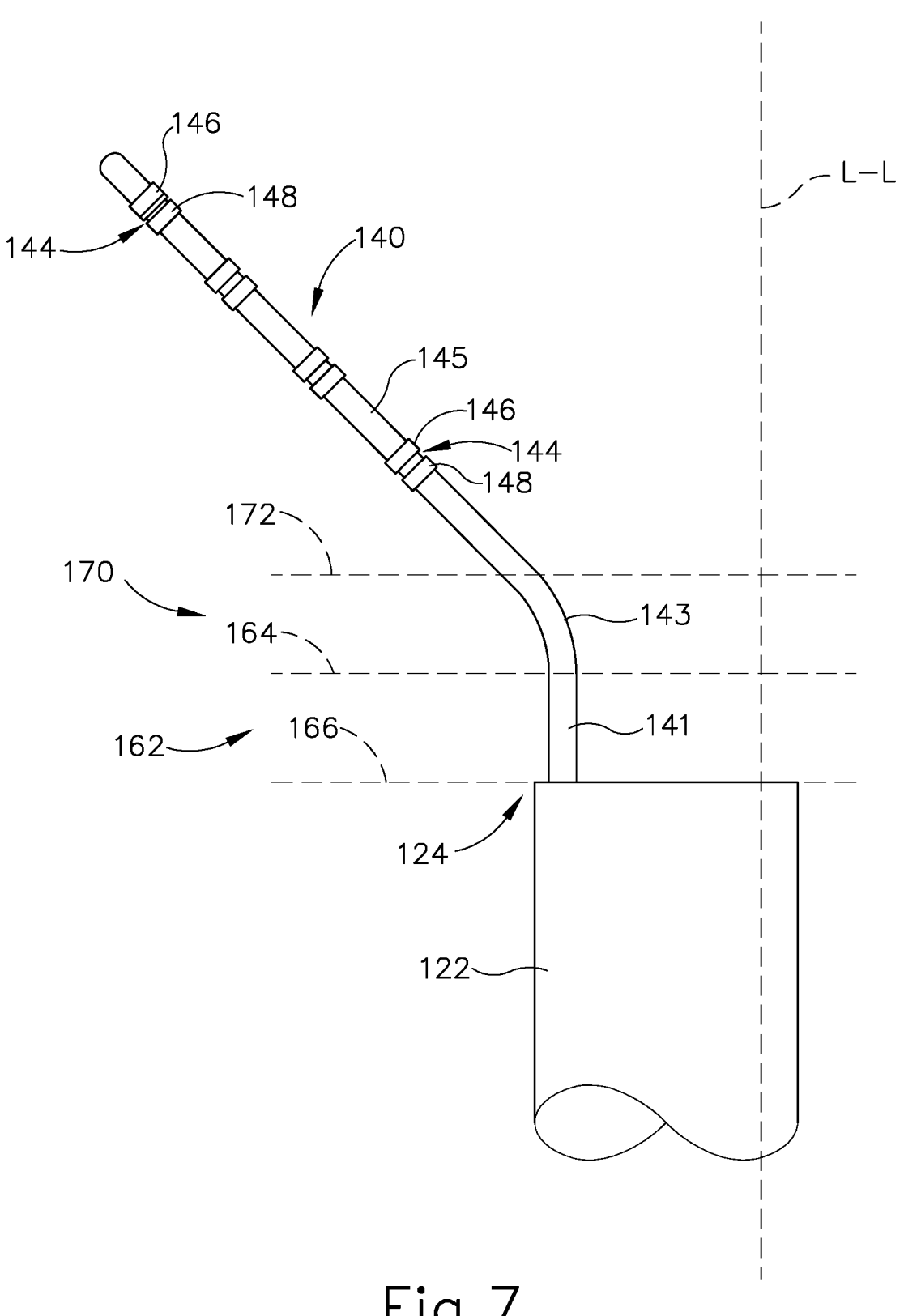
FIG. 7 depicts a partial side elevational view of the end effector of FIG. 3 with one arm in a three-segment configuration, and with the other arms omitted.

As shown in FIG. 7, arm (140) includes a first segment (141), a second segment (143), and a third segment (145). First segment (141) extends from distal end (124) of shaft (122), from proximal plane (166) to intermediate plane (164). First segment (141) is substantially straight and is parallel with the central longitudinal axis (L-L) of shaft (122). Thus, first segments (141) of the angularly spaced array of arms (140) will generally define a cylindrical portion (162) of a three-dimensional profile (160) as referred to above in the context of FIG. 5. Second segment (143) is distal to first segment (141) and extends from intermediate plane (164) to distal plane (172). Second segment (143) extends along a curve, bending away from the central longitudinal axis (L-L) of shaft (122). Thus, second segments (143) of the angularly spaced array of arms (140) will generally define a bellmouth-shaped frusto-conical portion (170) of a three-dimensional profile (160) as referred to above in the context of FIG. 5. Alternatively, second segments (143) may extend away from the central longitudinal axis (L-L) of shaft (122) along respective straight paths that are obliquely oriented relative the central longitudinal axis (L-L) of shaft (122), thereby generally defining a pyramid-shaped frusto-conical portion (190) of a three-dimensional profile (180) as referred to above in the context of FIG. 6. Third segment (145) is distal to second segment (143) and extends distally from distal plane (172). Third segment (145) extends along a straight path that is obliquely oriented relative the central longitudinal axis (L-L) of shaft (122). In versions where second segments (143) are straight rather than curved, the oblique angle defined between third segment (145) and the central longitudinal axis (L-L) of shaft (122) may be larger than the oblique angle defined between second segment (143) and the central longitudinal axis (L-L) of shaft (122).

In some other versions where arms (140) extend distally along respective straight paths at distal plane (172), these respective straight paths are parallel with the longitudinal axis (L-L) of catheter shaft (122). By way of example only, such a configuration may generally resemble the end effector (1130) shown in FIG. 16 and described below. In these versions, in versions similar to that depicted in FIG. 7, or in other configurations, it should be understood that arms (140) may continue to extend distally past distal plane (172), such that distal plane (172) should not be viewed as necessarily corresponding with the distal end of end effector (130).

In the present example, intermediate plane (164) represents the longitudinal position where arms (140) transition from being generally straight and parallel with each other to splaying outwardly away from each other along respective curves. The cross-sectional area (Ap) of the proximal plane (166) region of three-dimensional profile (160) is approximately equal to the cross-sectional area (Ai) of the intermediate plane (164) region of three-dimensional profile (160). The cross-sectional area (Ad) of the distal plane (172) region is larger than the cross-sectional area of the other planes (164, 166). While the cross-sectional areas (Ap, Ai, Ad) are shown as orthogonal with respect to the longitudinal axis (L-L) in the exemplary figures due to the configuration of arms (140) being symmetric about the longitudinal axis (L-L), the splaying of arms (140) does not necessarily have to be symmetrical with respect to the longitudinal axis (L-L) and therefore the proximal, intermediate and distal planes of the respective areas (Ap, Ai, Ad) may intersect each other or otherwise be non-orthogonal with respect to the longitudinal axis (L-L).

In the present example, central shaft (150) and ring electrode (154) are configured and positioned such that the longitudinal position of electrode (154) corresponds with cylindrical portion (162) of three-dimensional profile (160). Ring electrode (154) is thus proximally located in relation to intermediate plane (164). Ring electrode (154) may thus be regarded as being enshrouded by cylindrical portion (162) of three-dimensional profile (160) defined by arms (140) of end effector (130). In some other versions, central shaft (150) and ring electrode (154) are configured and positioned such that ring electrode (154) is longitudinally positioned between distal plane (172) and intermediate plane (164). In such versions, ring electrode (154) may be regarded as being enshrouded by bellmouth-shaped frusto-conical portion (170) of three-dimensional profile (160) defined by arms (140) of end effector (130).

By having ring electrode (154) enshrouded by bellmouth-shaped frusto-conical portion (170) or cylindrical portion (162) of three-dimensional profile (160) defined by spines or arms (140) of end effector (130), the flow of blood around ring electrode (154) may be relatively smooth, which may enable ring electrode (154) to pick up electrical potentials from the blood in a relatively reliable fashion. In other words, the arrangement of arms (140) around ring electrode (154) may affect the flow of blood around electrode (154) such that the flow is less turbulent than the flow otherwise might be if ring electrode (154) were positioned elsewhere; and such that the pickup of electrical potentials from the blood by ring electrode (154) is more reliable than it otherwise might be if ring electrode (154) were positioned elsewhere. The reduction in blood flow turbulence, and increase in sensing reliability by ring electrode (154), may be particularly enhanced when ring electrode (154) is enshrouded by cylindrical portion (164).

FIG. 6 shows another exemplary three-dimensional profile (180) that may be defined by at least proximal portions of arms (140). While arms (140) are omitted from FIG. 6, it should be understood that at least the proximal portions of arms (140) may be generally arranged around the boundary depicted as three-dimensional profile (180). In some versions, arms (140) are resiliently biased such that at least the proximal portions of arms (140) define three-dimensional profile (180). Three-dimensional profile (180) of this example includes cylindrical portion (162) and a pyramid-shaped frusto-conical portion (190). Cylindrical portion (162) is proximally bounded by a proximal plane (166) and distally bounded by an intermediate plane (164). Proximal plane (166) is located at distal end (124) of catheter shaft (122). Pyramid-shaped frusto-conical portion (190) is proximally bounded by intermediate plane (164) and distally bounded by distal plane (192).

In some versions, distal plane (192) is located at the free ends or distal tips of arms (140), such that arms (140) distally terminate at distal plane (192). In some other versions, arms (140) continue to extend distally along respective straight paths at distal plane (192), such that pyramid-shaped frusto-conical portion (190) represents an intermediate angled portion of each arm (140) that is longitudinally interposed between respective distal and proximal straight portions of each arm (140). In some versions where arms (140) extend distally along respective straight paths at distal plane (192), these respective straight paths are obliquely oriented away from the longitudinal axis (L-L) of catheter shaft (122) (e.g., at angles that are larger than the angles represented by pyramid-shaped frusto-conical portion (190). In some other versions where arms (140) extend distally along respective straight paths at distal plane (192), these respective straight paths are parallel with the longitudinal axis (L-L) of catheter shaft (122). In either case, or in other configurations, it should be understood that arms (140) may continue to extend distally past distal plane (192), such that distal plane (192) should not be viewed as necessarily corresponding with the distal end of end effector (130).

In the present example, intermediate plane (164) represents the longitudinal position where arms (140) transition from being generally straight and parallel with each other to splaying outwardly away from each other along respective oblique paths. The cross-sectional area of the proximal plane (166) region of three-dimensional profile (180) is approximately equal to the cross-sectional area of the intermediate plane (164) region of three-dimensional profile (180). The cross-sectional area of the distal plane (192) region is larger than the cross-sectional area of the other planes (164, 166).

In the present example, central shaft (150) and ring electrode (154) are configured and positioned such that the longitudinal position of electrode (154) corresponds with cylindrical portion (162) of three-dimensional profile (180). Ring electrode (154) is thus proximally located in relation to intermediate plane (164). Ring electrode (154) may thus be regarded as being enshrouded by cylindrical portion (162) of three-dimensional profile (180) defined by arms (140) of end effector (130). In some other versions, central shaft (150) and ring electrode (154) are configured and positioned such that ring electrode (154) is longitudinally positioned between distal plane (192) and intermediate plane (164). In such versions, ring electrode (154) may be regarded as being enshrouded by pyramid-shaped frusto-conical portion (190) of three-dimensional profile (180) defined by arms (140) of end effector (130).

By having ring electrode (154) enshrouded by pyramid-shaped frusto-conical portion (190) or cylindrical portion (162) of three-dimensional profile (190) defined by arms (140) of end effector (130), the flow of blood around ring electrode (154) may be relatively smooth, which may enable ring electrode (154) to pick up electrical potentials from the blood in a relatively reliable fashion. In other words, the arrangement of arms (140) around ring electrode (154) may affect the flow of blood around electrode (154) such that the flow is less turbulent than the flow otherwise might be if ring electrode (154) were positioned elsewhere; and such that the pickup of electrical potentials from the blood by ring electrode (154) is more reliable than it otherwise might be if ring electrode (154) were positioned elsewhere. The reduction in blood flow turbulence, and increase in sensing reliability by ring electrode (154), may be particularly enhanced when ring electrode (154) is enshrouded by cylindrical portion (162).

C. Exemplary Basket End Effector with Reference Electrode on Internal Shaft

Figures 8, 9:
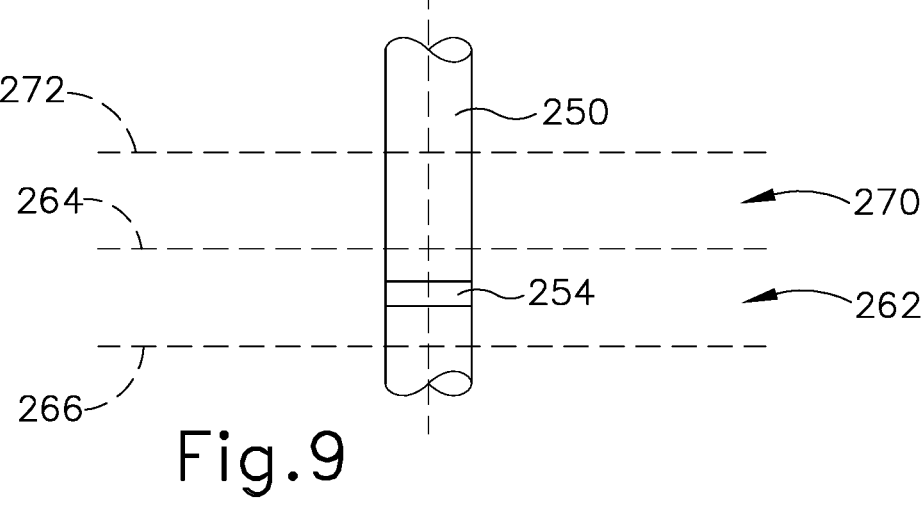
FIG. 8 depicts a side elevational view of an exemplary alternative end effector that may be incorporated into the catheter assembly of FIG. 1.
FIG. 9 depicts an enlarged side elevational view of a portion of a central shaft of the end effector of FIG. 8.

FIG. 8 shows another exemplary end effector (200) that may be incorporated into catheter assembly (100) in place of end effector (130). End effector (200) of this example includes an expandable assembly (220) that is formed by an angularly spaced array of beams (222). Each beam (222) includes four pairs (230) of bipolar electrodes (232, 234). Electrodes (232, 234) are each generally rectangular and are configured to pick up electrical potentials from tissue, just like electrodes (146, 148) described above. Electrodes (232, 234) may be used in a bipolar fashion or a unipolar fashion. The entirety of each electrode (232, 234) is confined to the outwardly presented surface of each beam (222) in the present example. Beams (222) thus have electrodes (232, 234) on only one side of each beam (222) (i.e., the tissue-contacting side of each beam (222)).

The proximal ends of beams (222) are positioned in an outer shaft (210), which may be considered as being analogous to catheter shaft (122) described above. The distal ends of beams (222) are coupled with a hub member (212). Hub member (212) is secured to a central inner shaft (250), which is coaxially positioned at the center of expandable assembly (220). Beams (222) are configured to transition expandable assembly (220) between a non-expanded state and an expanded state. The expanded state is shown in FIG. 8. When expandable assembly (220) is in the non-expanded state, beams (222) are urged inwardly to define an effective outer diameter that is less than or equal to the inner diameter of outer shaft (210). In some versions, beams (222) are resiliently biased to provide expandable assembly (220) in the expanded state. In some such versions, an outer sheath (214) is slidably disposed about outer shaft (210). When sheath (214) is in a distal position (e.g., such that the distal end of sheath (214) is distal to hub member (212)), sheath (214) constrains beams (222) inwardly, thereby maintaining expandable assembly (220) in the non-expanded state. When sheath (214) is in a proximal position (e.g., as shown in FIG. 8, such that the distal end of sheath (214) is proximal to expandable assembly (220)), beams (222) may resiliently provide expandable assembly (220) in the expanded state.

As another merely illustrative alternative, the state of expandable assembly (220) may be based on the relative longitudinal positioning of inner shaft (250) and outer shaft (210). In versions where inner shaft (250) is longitudinally stationary relative to handle (110), an actuator on handle (110) may drive outer shaft (210) proximally relative to inner shaft (250) to urge expandable assembly (220) to the non-expanded state; and drive outer shaft (210) distally relative to inner shaft (250) to urge expandable assembly (220) to the expanded state. In versions where outer shaft (210) is longitudinally stationary relative to handle (110), an actuator on handle (110) may drive inner shaft (250) distally relative to outer shaft (210) to urge expandable assembly (220) to the non-expanded state; and drive inner shaft (250) proximally relative to inner shaft (210) to urge expandable assembly (220) to the expanded state. Various suitable forms of inputs that may be provided on handle (110) to provide such actuation, as well as various suitable ways in which expandable assembly (220) may transition between the non-expanded state and the expanded state, will be apparent to those skilled in the art in view of the teachings herein.

As shown in FIG. 8, the configuration of end effector (200) may be considered in relation to three planes (264, 266, 272), which are perpendicular to the longitudinal axis (L-L) of shafts (210, 250). A proximal plane (266) is located at the distal end of shaft (210) and at the proximal end of end effector (200). An intermediate plane (264) is distal to proximal plane (266). A distal plane (272) is distal to intermediate plane (264). The longitudinal region of end effector (200) between planes (264, 266) may be regarded as a cylindrical portion (262) defining a cylindrical three-dimensional profile, much like cylindrical portion (162) described above in relation to FIGS. 5-6. Thus, the portions of beams (222) extending along cylindrical portion (262) may extend along respective straight paths that are parallel with the longitudinal axis (L-L) of shafts (210, 250). The longitudinal region of end effector (200) between planes (264, 272) may be regarded as a bellmouth-shaped frusto-conical portion (270) defining a bellmouth-shaped frusto-conical three-dimensional profile, much like bellmouth-shaped frusto-conical portion (170) described above in relation to FIG. 5. In the present example, the portions of beams (222) extending along bellmouth-shaped frusto-conical portion (270) extend along respective curved paths curving outwardly away from the longitudinal axis (L-L) of shafts (210, 250). The portions of beams (222) extending distally from distal plane (272) curve back inwardly toward the longitudinal axis (L-L) of shafts (210, 250), eventually leading to hub member (212). Distal plane (272) thus represents a transition of beams (222) from extending outwardly along respective curved paths to extending inwardly along respective curved paths.

Inner shaft (250) of this example includes a ring electrode (254), which is coaxially disposed about inner shaft (250) as shown in FIG. 9. In the present example, ring electrode (254) is longitudinally positioned between planes (264, 266), such that the longitudinal position of ring electrode (254) corresponds with the longitudinal position of cylindrical portion (262), and such that ring electrode (254) is enshrouded by cylindrical portion (262). In some other versions, ring electrode (254) is longitudinally positioned between planes (264, 272), such that the longitudinal position of ring electrode (254) corresponds with the longitudinal position of bellmouth-shaped frusto-conical portion (270), and such that ring electrode (254) is enshrouded by bellmouth-shaped frusto-conical portion (270).

Beams (222) are thus configured to prevent tissue from contacting ring electrode (254). Beams (222) nevertheless allow blood to flow through expandable assembly (220), thereby allowing blood to contact ring electrode (254). During use of end effector (200), one or more electrodes (232, 234) on beams (222) may contact a tissue surface (T) and thereby pick up electrical potentials at the contacted regions of the tissue surface (T), while ring electrode (254) picks up a reference potential from the blood in which ring electrode (254) is disposed. The processor of console (12) may process the potentials from electrodes (232, 234, 254) and thereby provide an electrocardiogram signal as described above.

By having ring electrode (254) enshrouded by bellmouth-shaped frusto-conical portion (270) or cylindrical portion (262) of the three-dimensional profile defined by beams (222) of end effector (200), the flow of blood around ring electrode (254) may be relatively smooth, which may enable ring electrode (254) to pick up electrical potentials from the blood in a relatively reliable fashion. In other words, the arrangement of beams (222) around ring electrode (254) may affect the flow of blood around electrode (254) such that the flow is less turbulent than the flow otherwise might be if ring electrode (254) were positioned elsewhere; and such that the pickup of electrical potentials from the blood by ring electrode (254) is more reliable than it otherwise might be if ring electrode (254) were positioned elsewhere. The reduction in blood flow turbulence, and increase in sensing reliability by ring electrode (254), may be particularly enhanced when ring electrode (254) is enshrouded by cylindrical portion (262).

D. Exemplary Multi-Arm End Effectors with Integral Reference Electrode

Figure 10:
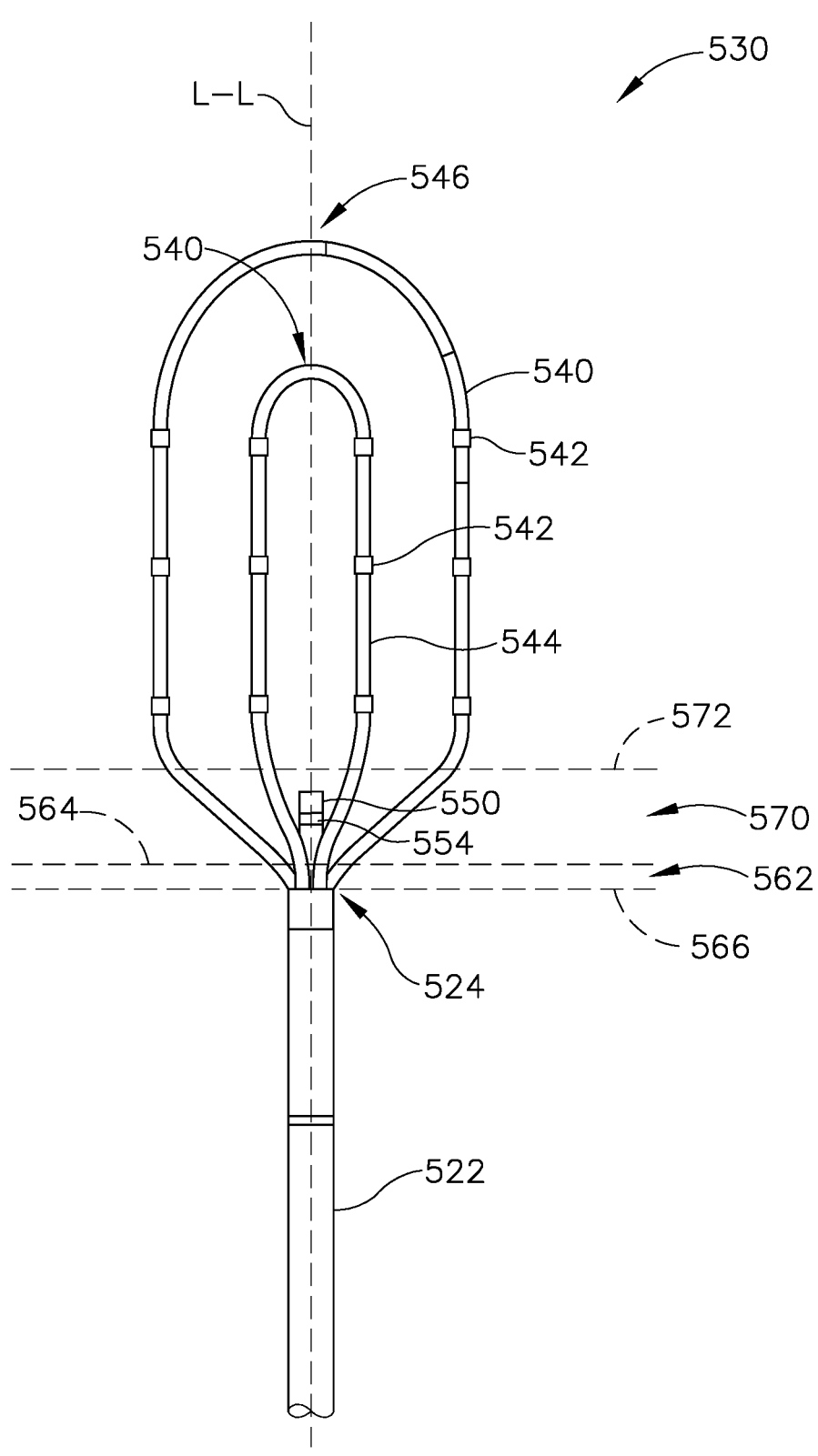
FIG. 10 depicts a side elevational view of another exemplary alternative end effector that may be incorporated into the catheter assembly of FIG. 1.

FIG. 10 shows another exemplary end effector (530) that may be incorporated into catheter assembly (100) in place of end effector (130). End effector (530) of this example includes an outer arm (540) and an outer arm (544). Arms (540, 544) extend distally from distal end (524) of catheter shaft (522). Arm (540) defines an outer loop while arm (544) defines an inner loop. The outer and inner loops are coupled to each other via a resilient joining member (546) at the distal end of each loop. Longitudinally intermediate regions of arms (540, 544) are parallel with each other. The proximal ends of arms (540, 544) converge at distal end (524) of catheter shaft (522).

Arms (540, 544) are positioned along a single flat plane in this example. However, arms (540, 544) are also flexible such that arms (540, 544) may be bent laterally away from a central longitudinal axis (L-L), along a path transverse to the plane defined by arms (540, 544), to thereby deform the plane defined by arms (540, 544). Such bending may occur when end effector (530) is pressed laterally against tissue. Arms (540, 544) may be resiliently biased to return to the flat, planar configuration shown in FIG. 10. In some other versions, portions of arms (540, 544) are further offset from each other such that arms (540, 544) are not positioned along a single flat plane.

The proximal ends of arms (540, 544) extend between a proximal plane (566) and an intermediate plane (564) along respective straight paths that are generally parallel with each other and that are generally parallel with the longitudinal axis (L-L) of catheter shaft (522). The proximal-most regions of arms (540, 544) between planes (564, 566) together define a generally rectangular first portion (562) of a profile of end effector (530). Distal to first portion (562), arms (540, 544) define a diverging second portion (570) of a profile of end effector (530). Second portion (570) extends from intermediate plane (564) to a distal plane (572). Arms (540, 544) thus extend outwardly along respective diverging paths through second portion (570). Distal to distal plane (572), arms (540, 544) extend along respective straight paths that are parallel with each other as noted above.

Each arm (540, 544) has a longitudinally spaced array of electrodes (542). Each electrode (542) is configured to contact tissue and thereby pick up electrical potentials from the contacted tissue. In some versions, electrodes (542) are provided in pairs like electrodes (146, 148) described above.

End effector (530) further includes a central inner shaft (550) having a ring electrode (554). Ring electrode (554) is coaxially disposed about inner shaft (550). In the present example, ring electrode (554) is longitudinally positioned between planes (564, 572), such that the longitudinal position of ring electrode (554) corresponds with the longitudinal position of second portion (570), and such that ring electrode (554) is enshrouded by second portion (570). In some other versions, ring electrode (554) is longitudinally positioned between planes (564, 566), such that the longitudinal position of ring electrode (554) corresponds with the longitudinal position of first portion (562), and such that ring electrode (554) is enshrouded by first portion (562).

With ring electrode (554) being enshrouded by first portion (562) or second portion (570), arms (540, 544) may generally prevent tissue from contacting ring electrode (554). Arms (540, 544) nevertheless allow blood to flow through end effector (530), thereby allowing blood to contact ring electrode (554). During use of end effector (530), one or more electrodes (542) on arms (540, 544) may contact a tissue surface (T) and thereby pick up electrical potentials at the contacted regions of the tissue surface (T), while ring electrode (554) picks up a reference potential from the blood in which ring electrode (554) is disposed. The processor of console (12) may process the potentials from electrodes (542, 554) and thereby provide an electrocardiogram signal as described above.

By having ring electrode (554) enshrouded by first portion (562) or second portion (570) of the profile defined by arms (540, 544) of end effector (530), the flow of blood around ring electrode (554) may be relatively smooth, which may enable ring electrode (554) to pick up electrical potentials from the blood in a relatively reliable fashion. In other words, the arrangement of arms (540, 544) around ring electrode (554) may affect the flow of blood around electrode (554) such that the flow is less turbulent than the flow otherwise might be if ring electrode (554) were positioned elsewhere; and such that the pickup of electrical potentials from the blood by ring electrode (554) is more reliable than it otherwise might be if ring electrode (554) were positioned elsewhere. The reduction in blood flow turbulence, and increase in sensing reliability by ring electrode (554), may be particularly enhanced when ring electrode (554) is enshrouded by first portion (562).

Figures 11, 12, 13:
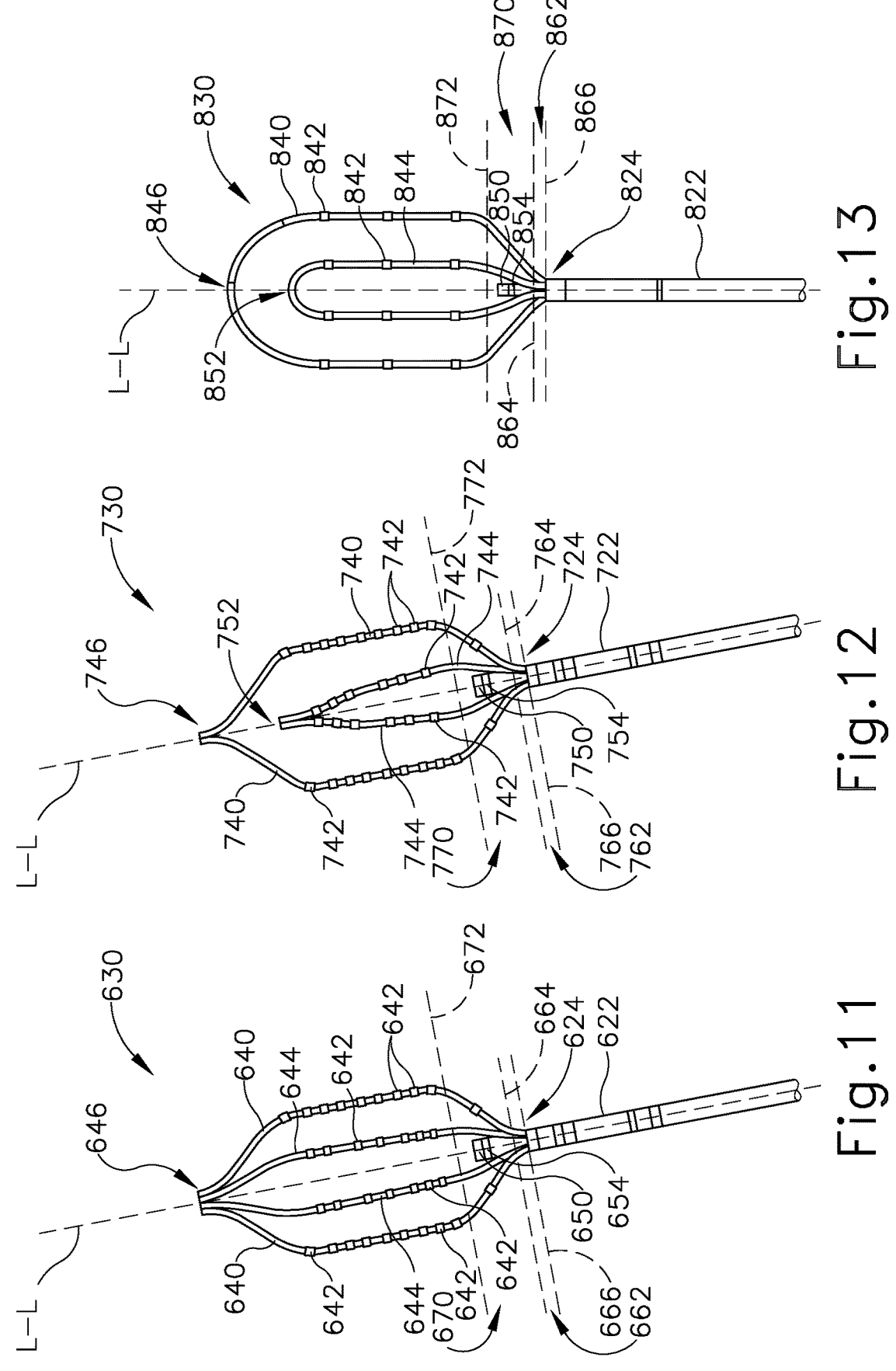
FIG. 11 depicts a side elevational view of another exemplary alternative end effector that may be incorporated into the catheter assembly of FIG. 1.
FIG. 12 depicts a side elevational view of another exemplary alternative end effector that may be incorporated into the catheter assembly of FIG. 1.
FIG. 13 depicts a side elevational view of another exemplary alternative end effector that may be incorporated into the catheter assembly of FIG. 1.

FIG. 11 shows another exemplary end effector (630) that may be incorporated into catheter assembly (100) in place of end effector (130). End effector (630) of this example includes a pair of outer arms (640) and a pair of inner arms (644). Arms (640, 644) extend distally from distal end (624) of catheter shaft (622) and distally terminate at a joint (646). In some versions, joint (646) is formed simply by welding, adhering, or otherwise securing the distal ends of arms (640, 644) together. Longitudinally intermediate regions of arms (640, 644) are parallel with each other. The proximal ends of arms (640, 644) converge at distal end (624) of catheter shaft (622) while the distal ends of arms (640, 644) generally converge at joint (646). Arms (640, 644) are all positioned along a single flat plane in this example. However, arms (640, 644) are also flexible such that arms (640, 644) may be bent laterally away from a central longitudinal axis (L-L), along a path transverse to the plane defined by arms (640, 644), to thereby deform the plane defined by arms (640, 644). Such bending may occur when end effector (630) is pressed laterally against tissue. Arms (640, 544) may be resiliently biased to return to the flat, planar configuration shown in FIG. 11. In some other versions, portions of arms (640, 644) are further offset from each other such that arms (640, 644) are not positioned along a single flat plane.

The proximal ends of arms (640, 644) extend between a proximal plane (666) and an intermediate plane (664) along respective straight paths that are generally parallel with each other and that are generally parallel with the longitudinal axis (L-L) of catheter shaft (622). The proximal-most regions of arms (640, 644) between planes (664, 666) together define a generally rectangular first portion (662) of a profile of end effector (630). Distal to first portion (662), arms (640, 644) define a diverging second portion (670) of a profile of end effector (630). Second portion (670) extends from intermediate plane (664) to a distal plane (672). Arms (640, 644) thus extend outwardly along respective diverging paths through second portion (670). Distal to distal plane (672), arms (640, 644) extend along respective straight paths that are parallel with each other as noted above.

Each arm (640, 644) has a longitudinally spaced array of electrodes (642). Each electrode (642) is configured to contact tissue and thereby pick up electrical potentials from the contacted tissue. In some versions, electrodes (642) are provided in pairs like electrodes (146, 148) described above.

End effector (630) further includes a central inner shaft (650) having a ring electrode (654). Ring electrode (654) is coaxially disposed about inner shaft (650). In the present example, ring electrode (654) is longitudinally positioned between planes (664, 672), such that the longitudinal position of ring electrode (654) corresponds with the longitudinal position of second portion (670), and such that ring electrode (654) is enshrouded by second portion (670). In some other versions, ring electrode (654) is longitudinally positioned between planes (664, 666), such that the longitudinal position of ring electrode (654) corresponds with the longitudinal position of first portion (662), and such that ring electrode (654) is enshrouded by first portion (662).

With ring electrode (654) being enshrouded by first portion (662) or second portion (670), arms (640, 644) may generally prevent tissue from contacting ring electrode (654). Arms (640, 644) nevertheless allow blood to flow through end effector (630), thereby allowing blood to contact ring electrode (654). During use of end effector (630), one or more electrodes (642) on arms (640, 644) may contact a tissue surface (T) and thereby pick up electrical potentials at the contacted regions of the tissue surface (T), while ring electrode (654) picks up a reference potential from the blood in which ring electrode (654) is disposed. The processor of console (12) may process the potentials from electrodes (642, 654) and thereby provide an electrocardiogram signal as described above.

By having ring electrode (654) enshrouded by first portion (662) or second portion (670) of the profile defined by arms (640, 644) of end effector (630), the flow of blood around ring electrode (654) may be relatively smooth, which may enable ring electrode (654) to pick up electrical potentials from the blood in a relatively reliable fashion. In other words, the arrangement of arms (640, 644) around ring electrode (654) may affect the flow of blood around electrode (654) such that the flow is less turbulent than the flow otherwise might be if ring electrode (654) were positioned elsewhere; and such that the pickup of electrical potentials from the blood by ring electrode (654) is more reliable than it otherwise might be if ring electrode (654) were positioned elsewhere. The reduction in blood flow turbulence, and increase in sensing reliability by ring electrode (654), may be particularly enhanced when ring electrode (654) is enshrouded by first portion (662).

FIG. 12 shows another exemplary end effector (730) that may be incorporated into catheter assembly (100) in place of end effector (130). End effector (730) of this example includes a pair of outer arms (740) and a pair of inner arms (744). Arms (740, 744) extend distally from distal end (724) of catheter shaft (722). Arms (740) distally terminate at a joint (746); while arms (744) distally terminate at a joint (752) that is proximal to joint (746). In some versions, each joint (746, 752) is formed simply by welding, adhering, or otherwise securing the distal ends of the corresponding arms (740, 744) together. Longitudinally intermediate regions of arms (740, 744) are generally parallel with each other. The proximal ends of arms (740, 744) converge at distal end (724) of catheter shaft (722) while the distal ends of arms (740, 744) converge at respective joints (746, 752). Arms (740, 744) are all positioned along a single flat plane in this example. However, arms (740, 744) are also flexible such that arms (740, 744) may be bent laterally away from a central longitudinal axis (L-L), along a path transverse to the plane defined by arms (740, 744), to thereby deform the plane defined by arms (740, 744). Such bending may occur when end effector (730) is pressed laterally against tissue. Arms (740, 744) may be resiliently biased to return to the flat, planar configuration shown in FIG. 12. In some other versions, portions of arms (740, 744) are further offset from each other such that arms (740, 744) are not positioned along a single flat plane.

The proximal ends of arms (740, 744) extend between a proximal plane (766) and an intermediate plane (764) along respective straight paths that are generally parallel with each other and that are generally parallel with the longitudinal axis (L-L) of catheter shaft (722). The proximal-most regions of arms (740, 744) between planes (764, 766) together define a generally rectangular first portion (762) of a profile of end effector (730). Distal to first portion (762), arms (740, 744) define a diverging second portion (770) of a profile of end effector (730). Second portion (770) extends from intermediate plane (764) to a distal plane (772). Arms (740, 744) thus extend outwardly along respective diverging paths through second portion (770). Distal to distal plane (772), arms (740, 744) extend along respective straight paths that are parallel with each other as noted above.

Each arm (740, 744) has a longitudinally spaced array of electrodes (742). Each electrode (742) is configured to contact tissue and thereby pick up electrical potentials from the contacted tissue. In some versions, electrodes (742) are provided in pairs like electrodes (146, 148) described above.

End effector (730) further includes a central inner shaft (750) having a ring electrode (754). Ring electrode (754) is coaxially disposed about inner shaft (750). In the present example, ring electrode (754) is longitudinally positioned between planes (764, 772), such that the longitudinal position of ring electrode (754) corresponds with the longitudinal position of second portion (770), and such that ring electrode (754) is enshrouded by second portion (770). In some other versions, ring electrode (754) is longitudinally positioned between planes (764, 766), such that the longitudinal position of ring electrode (754) corresponds with the longitudinal position of first portion (762), and such that ring electrode (754) is enshrouded by first portion (762).

With ring electrode (754) being enshrouded by first portion (762) or second portion (770), arms (740, 744) may generally prevent tissue from contacting ring electrode (754). Arms (740, 744) nevertheless allow blood to flow through end effector (730), thereby allowing blood to contact ring electrode (754). During use of end effector (730), one or more electrodes (742) on arms (740, 744) may contact a tissue surface (T) and thereby pick up electrical potentials at the contacted regions of the tissue surface (T), while ring electrode (754) picks up a reference potential from the blood in which ring electrode (754) is disposed. The processor of console (12) may process the potentials from electrodes (742, 754) and thereby provide an electrocardiogram signal as described above.

By having ring electrode (754) enshrouded by first portion (762) or second portion (770) of the profile defined by arms (740, 744) of end effector (730), the flow of blood around ring electrode (754) may be relatively smooth, which may enable ring electrode (754) to pick up electrical potentials from the blood in a relatively reliable fashion. In other words, the arrangement of arms (740, 744) around ring electrode (754) may affect the flow of blood around electrode (754) such that the flow is less turbulent than the flow otherwise might be if ring electrode (754) were positioned elsewhere; and such that the pickup of electrical potentials from the blood by ring electrode (754) is more reliable than it otherwise might be if ring electrode (754) were positioned elsewhere. The reduction in blood flow turbulence, and increase in sensing reliability by ring electrode (754), may be particularly enhanced when ring electrode (754) is enshrouded by first portion (762).

FIG. 13 shows another exemplary end effector (830) that may be incorporated into catheter assembly (100) in place of end effector (130). End effector (830) of this example includes an outer arm (840) and an inner arm (844). Arms (840, 844) extend distally from distal end (824) of catheter shaft (822). Arm (840) forms a distal bend (846); while arm (844) forms a distal bend (852) that is proximal to distal bend (846). Longitudinally intermediate regions of arms (840, 844) are generally parallel with each other. The proximal ends of arms (840, 844) converge at distal end (824) of catheter shaft (822). Arms (840, 844) are positioned along a single flat plane in this example. However, arms (840, 844) are also flexible such that arms (840, 844) may be bent laterally away from a central longitudinal axis (L-L), along a path transverse to the plane defined by arms (840, 844), to thereby deform the plane defined by arms (840, 844). Such bending may occur when end effector (830) is pressed laterally against tissue. Arms (840, 844) may be resiliently biased to return to the flat, planar configuration shown in FIG. 13. In some other versions, portions of arms (840, 844) are further offset from each other such that arms (840, 844) are not positioned along a single flat plane.

The proximal ends of arms (840, 844) extend between a proximal plane (866) and an intermediate plane (864) along respective straight paths that are generally parallel with each other and that are generally parallel with the longitudinal axis (L-L) of catheter shaft (822). The proximal-most regions of arms (840, 844) between planes (864, 866) together define a generally rectangular first portion (862) of a profile of end effector (830). Distal to first portion (862), arms (840, 844) define a diverging second portion (870) of a profile of end effector (830). Second portion (870) extends from intermediate plane (864) to a distal plane (872). Arms (840, 844) thus extend outwardly along respective diverging paths through second portion (870). Distal to distal plane (872), arms (840, 844) extend along respective straight paths that are parallel with each other as noted above.

Each arm (840, 844) has a longitudinally spaced array of electrodes (842). Each electrode (842) is configured to contact tissue and thereby pick up electrical potentials from the contacted tissue. In some versions, electrodes (842) are provided in pairs like electrodes (146, 148) described above.

End effector (830) further includes a central inner shaft (850) having a ring electrode (854). Ring electrode (854) is coaxially disposed about inner shaft (850). In the present example, ring electrode (854) is longitudinally positioned between planes (864, 872), such that the longitudinal position of ring electrode (854) corresponds with the longitudinal position of second portion (870), and such that ring electrode (854) is enshrouded by second portion (870). In some other versions, ring electrode (854) is longitudinally positioned between planes (864, 866), such that the longitudinal position of ring electrode (854) corresponds with the longitudinal position of first portion (862), and such that ring electrode (854) is enshrouded by first portion (862).

With ring electrode (854) being enshrouded by first portion (862) or second portion (870), arms (840, 844) may generally prevent tissue from contacting ring electrode (854). Arms (840, 844) nevertheless allow blood to flow through end effector (830), thereby allowing blood to contact ring electrode (854). During use of end effector (830), one or more electrodes (842) on arms (840, 844) may contact a tissue surface (T) and thereby pick up electrical potentials at the contacted regions of the tissue surface (T), while ring electrode (854) picks up a reference potential from the blood in which ring electrode (854) is disposed. The processor of console (12) may process the potentials from electrodes (842, 854) and thereby provide an electrocardiogram signal as described above.

By having ring electrode (854) enshrouded by first portion (862) or second portion (870) of the profile defined by arms (840, 844) of end effector (830), the flow of blood around ring electrode (854) may be relatively smooth, which may enable ring electrode (854) to pick up electrical potentials from the blood in a relatively reliable fashion. In other words, the arrangement of arms (840, 844) around ring electrode (854) may affect the flow of blood around electrode (854) such that the flow is less turbulent than the flow otherwise might be if ring electrode (854) were positioned elsewhere; and such that the pickup of electrical potentials from the blood by ring electrode (854) is more reliable than it otherwise might be if ring electrode (854) were positioned elsewhere. The reduction in blood flow turbulence, and increase in sensing reliability by ring electrode (854), may be particularly enhanced when ring electrode (854) is enshrouded by first portion (862).

Figures 14, 15:
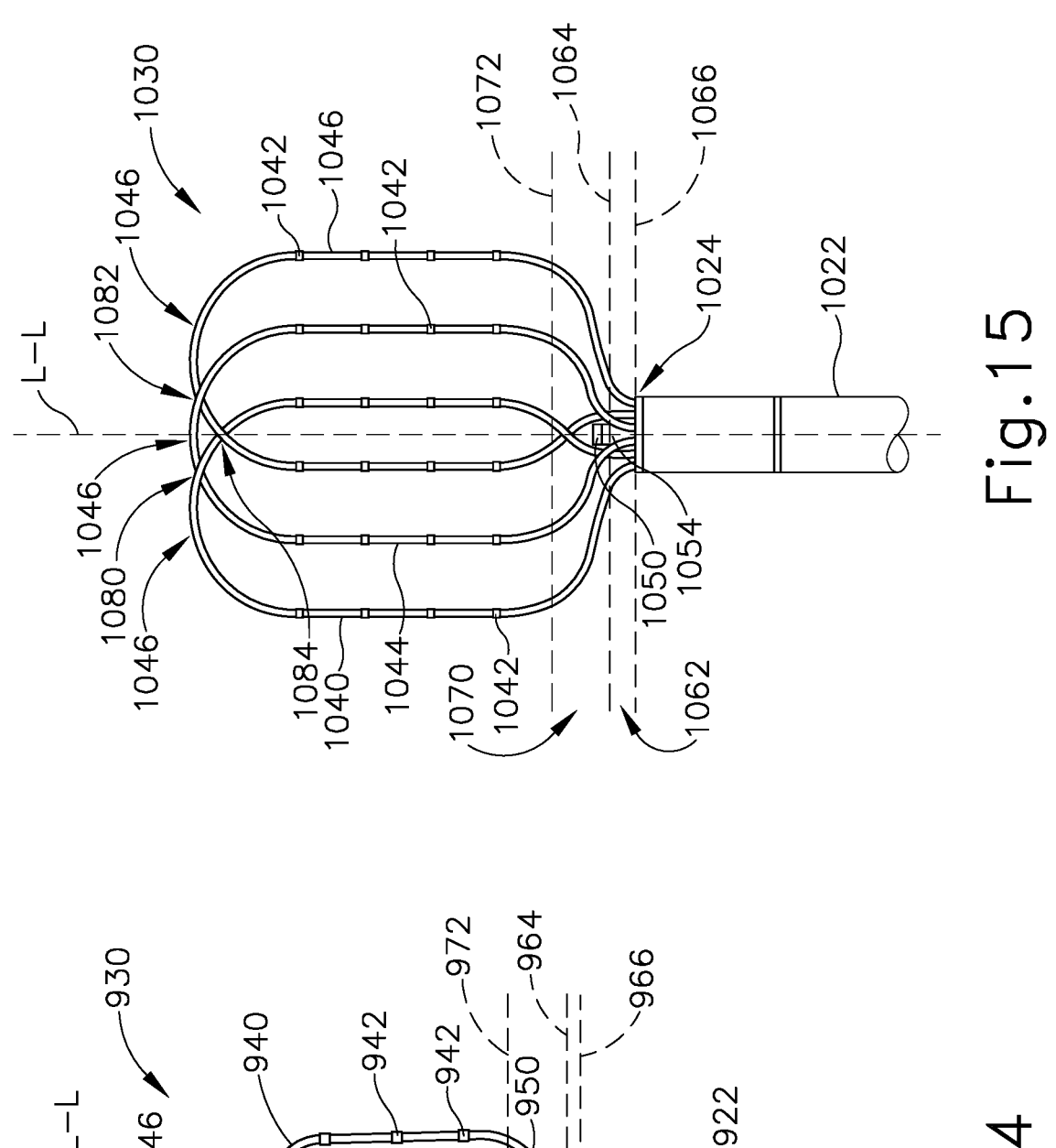
FIG. 14 depicts a side elevational view of another exemplary alternative end effector that may be incorporated into the catheter assembly of FIG. 1.
FIG. 15 depicts a side elevational view of another exemplary alternative end effector that may be incorporated into the catheter assembly of FIG. 1.

FIG. 14 shows another exemplary end effector (930) that may be incorporated into catheter assembly (100) in place of end effector (130). End effector (930) of this example includes a first arm (940) and a second arm (944). Arms (940, 944) extend distally from distal end (924) of catheter shaft (922). Each arm (940) forms a respective distal bend (946), with distal bends (946) being located at the same longitudinal distance from distal end (924) of catheter shaft (922). Arms (940, 944) overlap each other at an overlap point (980). Longitudinally intermediate regions of arms (940, 944) are generally parallel with each other. The proximal ends of arms (940, 944) converge at distal end (924) of catheter shaft (922). Arm (940) is positioned along a first flat plane in this example. Arm (944) is positioned along a second flat plane in this example, slightly offset from the first plane of arm (940). Arms (940, 944) are also flexible such that arms (940, 944) may be bent laterally away from a central longitudinal axis (L-L), along a path transverse to the planes defined by arms (940, 944), to thereby deform the planes defined by arms (940, 944). Such bending may occur when end effector (930) is pressed laterally against tissue. Arms (940, 944) may be resiliently biased to return to the flat, planar configuration shown in FIG. 14. In some other versions, portions of arms (940, 944) are further offset from each other such that arms (940, 944) are not positioned along a single flat plane.

The proximal ends of arms (940, 944) extend between a proximal plane (966) and an intermediate plane (964) along respective straight paths that are generally parallel with each other and that are generally parallel with the longitudinal axis (L-L) of catheter shaft (922). The proximal-most regions of arms (940, 944) between planes (964, 966) together define a generally rectangular first portion (962) of a profile of end effector (930). Distal to first portion (962), arms (940, 944) define a diverging second portion (970) of a profile of end effector (930). Second portion (970) extends from intermediate plane (964) to a distal plane (972). Arms (940, 944) thus extend outwardly along respective diverging paths through second portion (970). Distal to distal plane (972), arms (940, 944) extend along respective straight paths that are parallel with each other as noted above.

Each arm (940, 944) has a longitudinally spaced array of electrodes (942). Each electrode (942) is configured to contact tissue and thereby pick up electrical potentials from the contacted tissue. In some versions, electrodes (942) are provided in pairs like electrodes (146, 148) described above.

End effector (930) further includes a central inner shaft (950) having a ring electrode (954). Ring electrode (954) is coaxially disposed about inner shaft (950). In the present example, ring electrode (954) is longitudinally positioned between planes (964, 972), such that the longitudinal position of ring electrode (954) corresponds with the longitudinal position of second portion (970), and such that ring electrode (954) is enshrouded by second portion (970). In some other versions, ring electrode (954) is longitudinally positioned between planes (964, 966), such that the longitudinal position of ring electrode (954) corresponds with the longitudinal position of first portion (962), and such that ring electrode (954) is enshrouded by first portion (962).

With ring electrode (954) being enshrouded by first portion (962) or second portion (970), arms (940, 944) may generally prevent tissue from contacting ring electrode (954). Arms (940, 944) nevertheless allow blood to flow through end effector (930), thereby allowing blood to contact ring electrode (954). During use of end effector (930), one or more electrodes (942) on arms (940, 944) may contact a tissue surface (T) and thereby pick up electrical potentials at the contacted regions of the tissue surface (T), while ring electrode (954) picks up a reference potential from the blood in which ring electrode (954) is disposed. The processor of console (12) may process the potentials from electrodes (942, 954) and thereby provide an electrocardiogram signal as described above.

By having ring electrode (954) enshrouded by first portion (962) or second portion (970) of the profile defined by arms (940, 944) of end effector (930), the flow of blood around ring electrode (954) may be relatively smooth, which may enable ring electrode (954) to pick up electrical potentials from the blood in a relatively reliable fashion. In other words, the arrangement of arms (940, 944) around ring electrode (954) may affect the flow of blood around electrode (954) such that the flow is less turbulent than the flow otherwise might be if ring electrode (954) were positioned elsewhere; and such that the pickup of electrical potentials from the blood by ring electrode (954) is more reliable than it otherwise might be if ring electrode (954) were positioned elsewhere. The reduction in blood flow turbulence, and increase in sensing reliability by ring electrode (954), may be particularly enhanced when ring electrode (954) is enshrouded by first portion (962).

FIG. 15 shows another exemplary end effector (1030) that may be incorporated into catheter assembly (100) in place of end effector (130). End effector (1030) of this example includes a first arm (1040), a second arm (1044), and a third arm (1046). Arms (1040, 1044, 1046) extend distally from distal end (1024) of catheter shaft (1022). Each arm (1040) forms a respective distal bend (1046), with distal bends (1046) being located at the same longitudinal distance from distal end (1024) of catheter shaft (1022). Arms (1040, 1044) overlap each other at an overlap point (1080). Arms (1040, 1046) overlap each other at an overlap point (1084). Arms (1044, 1046) overlap each other at an overlap point (1082). Longitudinally intermediate regions of arms (1040, 1044, 1046) are generally parallel with each other. The proximal ends of arms (1040, 1044, 1046) converge at distal end (1024) of catheter shaft (1022). Arm (1040) is positioned along a first flat plane in this example. Arm (1044) is positioned along a second flat plane in this example, slightly offset from the first plane of arm (1040). Arm (1046) is positioned along a third flat plane in this example, slightly offset from the first and second planes of arm (1040, 1044).

Arms (1040, 1044, 1046) are also flexible such that arms (1040, 1044, 1046) may be bent laterally away from a central longitudinal axis (L-L), along a path transverse to the planes defined by arms (1040, 1044, 1046), to thereby deform the planes defined by arms (1040, 1044, 1046). Such bending may occur when end effector (1030) is pressed laterally against tissue. Arms (1040, 1044, 1046) may be resiliently biased to return to the flat, planar configuration shown in FIG. 15. In some other versions, portions of arms (1040, 1044, 1046) are further offset from each other such that arms (1040, 1044, 1046) are not positioned along a single flat plane.

The proximal ends of arms (1040, 1044, 1046) extend between a proximal plane (1066) and an intermediate plane (1064) along respective straight paths that are generally parallel with each other and that are generally parallel with the longitudinal axis (L-L) of catheter shaft (1022). The proximal-most regions of arms (1040, 1044, 1046) between planes (1064, 1066) together define a generally rectangular first portion (1062) of a profile of end effector (1030). Distal to first portion (1062), arms (1040, 1044, 1046) define a diverging second portion (1070) of a profile of end effector (1030). Second portion (1070) extends from intermediate plane (1064) to a distal plane (1072). Arms (1040, 1044, 1046) thus extend outwardly along respective diverging paths through second portion (1070). Distal to distal plane (1072), arms (1040, 1044, 1046) extend along respective straight paths that are parallel with each other as noted above.

Each arm (1040, 1044, 1046) has a longitudinally spaced array of electrodes (1042). Each electrode (1042) is configured to contact tissue and thereby pick up electrical potentials from the contacted tissue. In some versions, electrodes (1042) are provided in pairs like electrodes (146, 148) described above.

End effector (1030) further includes a central inner shaft (1050) having a ring electrode (1054). Ring electrode (1054)

is coaxially disposed about inner shaft (1050). In the present example, ring electrode (1054) is longitudinally positioned between planes (1064, 1072), such that the longitudinal position of ring electrode (1054) corresponds with the longitudinal position of second portion (1070), and such that ring electrode (1054) is enshrouded by second portion (1070). In some other versions, ring electrode (1054) is longitudinally positioned between planes (1064, 1066), such that the longitudinal position of ring electrode (1054) corresponds with the longitudinal position of first portion (1062), and such that ring electrode (1054) is enshrouded by first portion (1062).

With ring electrode (1054) being enshrouded by first portion (1062) or second portion (1070), arms (1040, 1044, 1046) may generally prevent tissue from contacting ring electrode (1054). Arms (1040, 1044, 1046) nevertheless allow blood to flow through end effector (1030), thereby allowing blood to contact ring electrode (1054). During use of end effector (1030), one or more electrodes (1042) on arms (1040, 1044, 1046) may contact a tissue surface (T) and thereby pick up electrical potentials at the contacted regions of the tissue surface (T), while ring electrode (1054) picks up a reference potential from the blood in which ring electrode (1054) is disposed. The processor of console (12) may process the potentials from electrodes (1042, 1054) and thereby provide an electrocardiogram signal as described above.

By having ring electrode (1054) enshrouded by first portion (1062) or second portion (1070) of the profile defined by arms (1040, 1044, 1046) of end effector (1030), the flow of blood around ring electrode (1054) may be relatively smooth, which may enable ring electrode (1054) to pick up electrical potentials from the blood in a relatively reliable fashion. In other words, the arrangement of arms (1040, 1044, 1046) around ring electrode (1054) may affect the flow of blood around electrode (1054) such that the flow is less turbulent than the flow otherwise might be if ring electrode (1054) were positioned elsewhere; and such that the pickup of electrical potentials from the blood by ring electrode (1054) is more reliable than it otherwise might be if ring electrode (1054) were positioned elsewhere. The reduction in blood flow turbulence, and increase in sensing reliability by ring electrode (1054), may be particularly enhanced when ring electrode (1054) is enshrouded by first portion (1062).

Figures 16, 17:
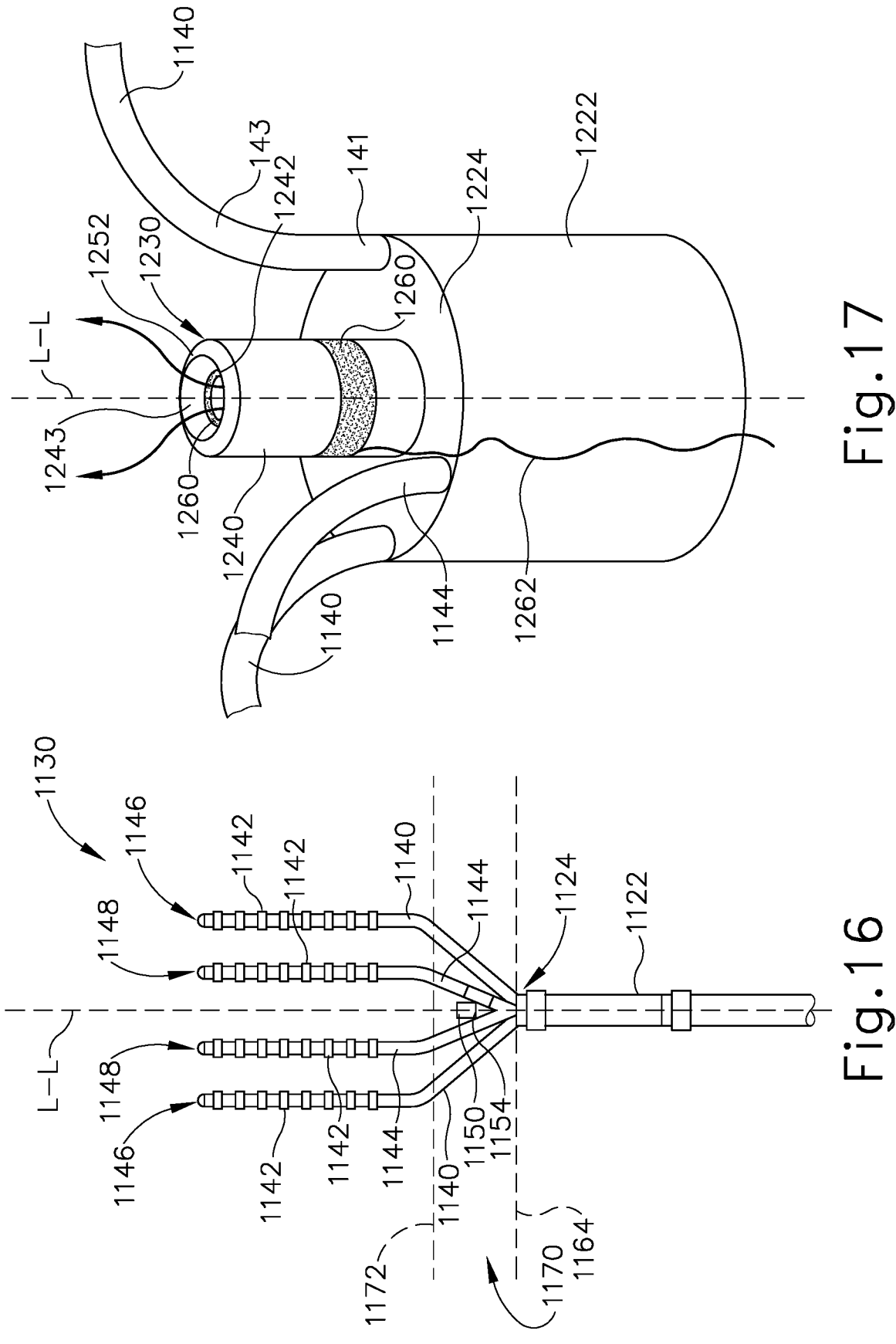
FIG. 16 depicts a side elevational view of another exemplary alternative end effector that may be incorporated into the catheter assembly of FIG. 1.
FIG. 17 depicts an enlarged perspective view of the tip that may be incorporated into the catheter assembly of FIGS. 10-16.

FIG. 16 shows another exemplary end effector (1130) that may be incorporated into catheter assembly (100) in place of end effector (130). End effector (1130) of this example includes a pair of outer arms (1140) and a pair of outer arms (1144). Arms (1140, 1444) extend distally from distal end (1124) of catheter shaft (1122). Each arm (1140) distally terminates at a free end (1146). Longitudinally intermediate and distal regions of arms (1140, 1444) are generally parallel with each other. The proximal ends of arms (1140, 1444) converge at distal end (1124) of catheter shaft (1122). Arms (1140, 1444) are positioned along a single flat plane in this example. However, arms (1140, 1444) are also flexible such that arms (1140, 1444) may be bent laterally away from a central longitudinal axis (L-L), along a path transverse to the plane defined by arms (1140, 1444), to thereby deform the plane defined by arms (1140, 1444). Such bending may occur when end effector (1130) is pressed laterally against tissue. Arms (1140, 1444) may be resiliently biased to return to the flat, planar configuration shown in FIG. 16. In some other versions, portions of arms (1140, 1444) are further offset from each other such that arms (1140, 1444) are not positioned along a single flat plane.

The proximal ends of arms (1140, 1444) extend between a proximal plane (1164) and a distal plane (1172) along respective paths that diverge outwardly away from each other and away from the longitudinal axis (L-L) of catheter shaft (1122). The proximal-most regions of arms (1140, 1444) between planes (1164, 1172) together thus define a diverging portion (1170) of a profile of end effector (1130). Distal to distal plane (1172), arms (1140, 1444) extend along respective straight paths that are parallel with each other as noted above.

Each arm (1140, 1444) has a longitudinally spaced array of electrodes (1142). Each electrode (1142) is configured to contact tissue and thereby pick up electrical potentials from the contacted tissue. In some versions, electrodes (1142) are provided in pairs like electrodes (146, 148) described above.

End effector (1130) further includes a central inner shaft (1150) having a ring electrode (1154). Ring electrode (1154) is coaxially disposed about inner shaft (1150). In the present example, ring electrode (1154) is longitudinally positioned between planes (1164, 1172), such that the longitudinal position of ring electrode (1154) corresponds with the longitudinal position of diverging portion (1170), and such that ring electrode (1154) is enshrouded by diverging portion (1170).

With ring electrode (1154) being enshrouded by diverging portion (1170), arms (1140, 1444) may generally prevent tissue from contacting ring electrode (1154). Arms (1140, 1444) nevertheless allow blood to flow through end effector (1130), thereby allowing blood to contact ring electrode (1154). During use of end effector (1130), one or more electrodes (1142) on arms (1140, 1444) may contact a tissue surface (T) and thereby pick up electrical potentials at the contacted regions of the tissue surface (T), while ring electrode (1154) picks up a reference potential from the blood in which ring electrode (1154) is disposed. The processor of console (12) may process the potentials from electrodes (1142, 1154) and thereby provide an electrocardiogram signal as described above.

By having ring electrode (1154) enshrouded by diverging portion (1170) of the profile defined by arms (1140, 1444) of end effector (1130), the flow of blood around ring electrode (1154) may be relatively smooth, which may enable ring electrode (1154) to pick up electrical potentials from the blood in a relatively reliable fashion. In other words, the arrangement of arms (1140, 1444) around ring electrode (1154) may affect the flow of blood around electrode (1154) such that the flow is less turbulent than the flow otherwise might be if ring electrode (1154) were positioned elsewhere; and such that the pickup of electrical potentials from the blood by ring electrode (1154) is more reliable than it otherwise might be if ring electrode (1154) were positioned elsewhere. The reduction in blood flow turbulence, and increase in sensing reliability by ring electrode (1154), may be particularly enhanced when ring electrode (1154) is enshrouded by diverging portion (1170).

By way of further example only, in addition to having the above-described features and functionalities, any of the foregoing end effectors (130, 200, 530, 630, 530, 730, 830, 930, 1030, 1130) may be constructed and operable in accordance with at least some of the teachings of U.S. Pub. No. 2016/0374753, entitled "Catheter Having Closed Loop Array with In-Plane Linear Electrode Portion," published December 29, 2016, the disclosure of which is incorporated by reference herein; U.S. Pub. No. 2018/0056038, entitled "Catheter with Bipole Electrode Spacer and Related Methods," published Mar. 1, 2018, the disclosure of which is incorporated by reference herein; U.S. Pat. No. 9,907,480, entitled "Catheter Spine Assembly with Closely-Spaced Bipole Microelectrodes," issued Mar. 6, 2018, the disclosure of which is incorporated by reference herein; U.S. Pat. No. 9,949,656, entitled "Catheter with Stacked Spine Electrode Assembly," issued Apr. 24, 2018, the disclosure of which is incorporated by reference herein; or U.S. Pat. No. 9,820, 664, entitled "Catheter with High Density Electrode Spine Array," issued Nov. 21, 2017, the disclosure of which is incorporated by reference herein.

E. Exemplary Irrigating Ablation Tip End Effector with Integral Reference Electrode FIG. 17 shows an enlarged perspective view of an end effector (1230) with tip (1240) that may be incorporated into catheter assembly (100). By way of further example only, end effector (1230) may be provided in place of central shaft (150) for the examples shown in FIGS. 3-6 or in place of central inner shafts (550, 650, 750, 850, 950, 1050, 1150) for the examples shown in FIGS. 10-16. End effector (1230) of this example includes an irrigating tip (1240) positioned at a distal end (1224) of a catheter shaft (1222). Irrigating tip (1240) defines a hollow interior and includes a main opening (1242) located contiguous to an end (1252) of irrigating tip (1240). An irrigation lumen (not shown) is provided for the main opening (1242) that extends along the length of catheter shaft (1222) and is in fluid communication with the hollow interior (1243) of irrigating tip (1240). Irrigation fluid communicated from the irrigation lumen to the hollow interior of irrigating tip (1240) will be expelled through main opening (1242).

While the reference electrode (1260) is shown as being proximal to the distal end of irrigating tip (1240) in FIG. 17 and on the outside surface of tip (1240), it is within the scope of this application to have a reference electrode (1260) positioned in the hollow interior (1243) of irrigating tip (1240). Wiring (1262) for electrode (1260) may be embedded in the extruded tip or suitably mounted to the irrigating lumen. In versions where reference electrode (1260) is recessed in hollow interior (1243), reference electrode (1260) remains exposed within hollow interior (1243) of irrigating tip (1240) such that blood may enter hollow interior (1243) of irrigating tip (1240) via main opening (1242) and contact reference electrode (1260). Alternatively, saline or some other fluid may contact reference electrode (1260) and thereby provide a reference potential to reference electrode (1260). As intended herein, the reference electrode is not capable of contacting tissue (T). Reference electrode (1260) may pick up a reference potential from blood, saline, or other fluid that passes through hollow interior (1243) of irrigating tip (1240). During use of end effector (1230), the reference electrode (1260) picks up a reference potential from the blood or saline, etc. that enters hollow interior (1243) of irrigating tip (1240) (e.g., via opening (1242) or otherwise). The processor of console (12) may process the potentials from irrigating tip (1240) and reference electrode (1260) and thereby provide an electrocardiogram signal as described above.

When reference electrode (1260) is used to pick up a reference potential from blood or saline that enters hollow interior (1243) of irrigating tip (1240) via opening (1242), the operator may cease communication of irrigation fluid to irrigating tip (1240) to thereby allow the blood to enter tip opening (1242). In some versions, suction is briefly communicated to irrigating tip (1240) to draw blood into the hollow interior (1243) of irrigating tip (1240) via lateral openings (1242). By way of example only, a separate suction lumen (not shown) may extend along catheter shaft (1222). Alternatively, the irrigation lumen may be operable to alternate between a state in which irrigation fluid is communicated to irrigating tip (1240) and a state in which suction is communicated to irrigating tip (1240). In versions where suction is provided via irrigating tip (1240), such suction may be very brief—just long enough to draw a sufficient amount of blood into the hollow interior of irrigating tip (1240) via lateral openings (1242) to contact reference electrode (1260) for a sufficient duration to pick up a reference potential from the blood. Various ways in which suction may be incorporated into end effector (1230) will be apparent to those skilled in the art in view of the teachings herein. Alternatively, end effector (1230) may completely lack suction capability.

Figure 18:
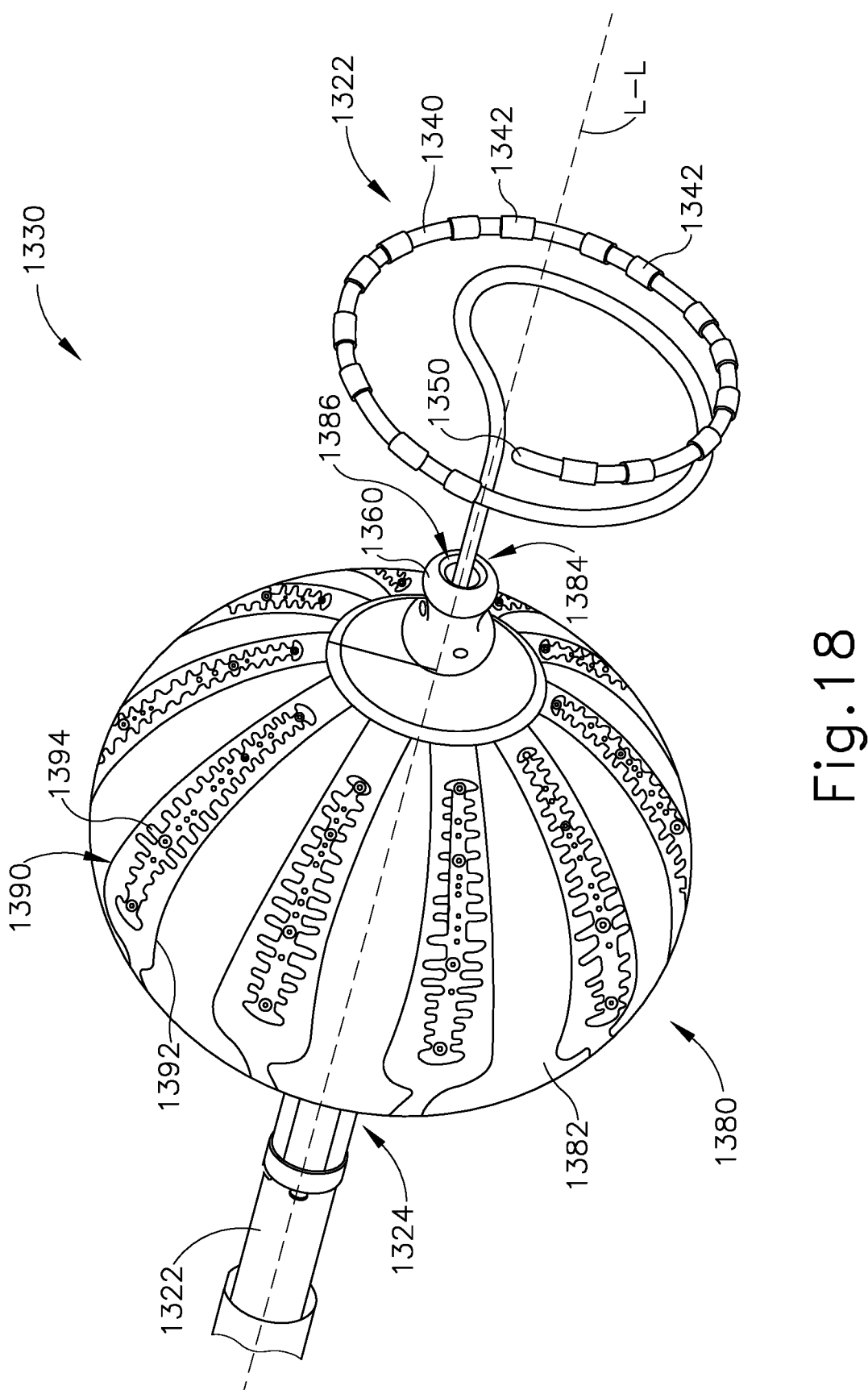
FIG. 18 depicts a perspective view of another exemplary alternative end effector that may be incorporated into the catheter assembly of FIG. 1.

F. Exemplary Lasso Tip End Effector with Expandable Ablation Element and Integral Reference Electrode FIG. 18 shows another exemplary end effector (1330) that may be incorporated into catheter assembly (100) in place of end effector (130). End effector (1330) of this example includes an expandable assembly (1380) and a lasso catheter (1332). Expandable assembly (1380) is positioned at a distal end (1324) of a catheter shaft (1322). Expandable assembly (1380) includes an expandable balloon (1382) (shown in an expanded state in FIG. 18) and an angularly spaced array of flex circuit assemblies (1390). Each flex circuit assembly (1390) includes a flexible substrate (1392) that is secured to balloon (1382). Each flex circuit assembly (1390) further includes an electrode (1394) secured to the corresponding flexible substrate (1392). Electrodes (1394) are operable to apply RF energy to tissue to thereby ablate the tissue. A hub member (1384) is secured to the distal end of balloon (1382). Flex circuit assemblies (1390) distally terminate at hub member (1384).

Lasso catheter (1332) is coaxially disposed in catheter shaft (1322) and expandable assembly (1380) and extends distally through a central opening (1386) formed in hub member (1384) of expandable assembly (1380). In some versions, lasso catheter (1332) is translatable relative to expandable assembly (1380) to thereby enable selective proximal retraction and distal extension of lasso catheter (1332) relative to expandable assembly. Lasso catheter (1332) includes a flexible body (1340) distally terminating in a tip (1350). Body (1340) is resiliently biased to assume the coiled configuration shown in FIG. 18. A plurality of electrodes (1342) are longitudinally spaced apart from each other along the coiled portion of body (1340). Electrodes (1342) are operable to contact tissue (T) and thereby pick up electrical potentials from the contacted tissue (T).

A ring electrode (1360) is positioned on hub member (1384) of expandable assembly (1380). While ring electrode (1360) is shown as being positioned on the distal-most portion of hub member (1384), ring electrode (1360) may instead be positioned at a proximal or longitudinally-intermediate portion of hub member (1384). Ring electrode (1360) is configured to contact blood that surrounds end effector (1330) and thereby pick up a reference potential from the blood. Ring electrode (1360) is further positioned and configured to avoid contact with tissue (T) during normal use of end effector (1330). In some other variations, ring electrode (1360) is positioned within an interior region of expandable assembly (1380). In such versions, blood may enter the interior region of expandable assembly (1380) via central opening (1386) of hub member (1384) and thereby contact electrode (1360). In such versions (among other versions), ring electrode (1360) need not necessarily be formed as a ring and may instead take any other suitable form.

During normal use of end effector (1330), one or more electrodes (1342) of lasso catheter (1332) may contact a tissue surface (T) and thereby pick up electrical potentials at the contacted regions of the tissue surface (T), while ring electrode (1360) picks up a reference potential from the blood that contacts ring electrode (1360). The processor of console (12) may process the potentials from electrodes (1342, 1360) and thereby provide an electrocardiogram signal as described above.

By way of further example only, in addition to having the above-described features and functionalities, end effector (1330) may be constructed and operable in accordance with at least some of the teachings of U.S. Pub. No. 2017/0312022, entitled "Irrigated Balloon Catheter with Flexible Circuit Electrode Assembly," published Nov. 2, 2017, the disclosure of which is incorporated by reference herein.

G. Exemplary Multi-Ray End Effector with Recessed Proximal Reference Electrode

Figure 19:
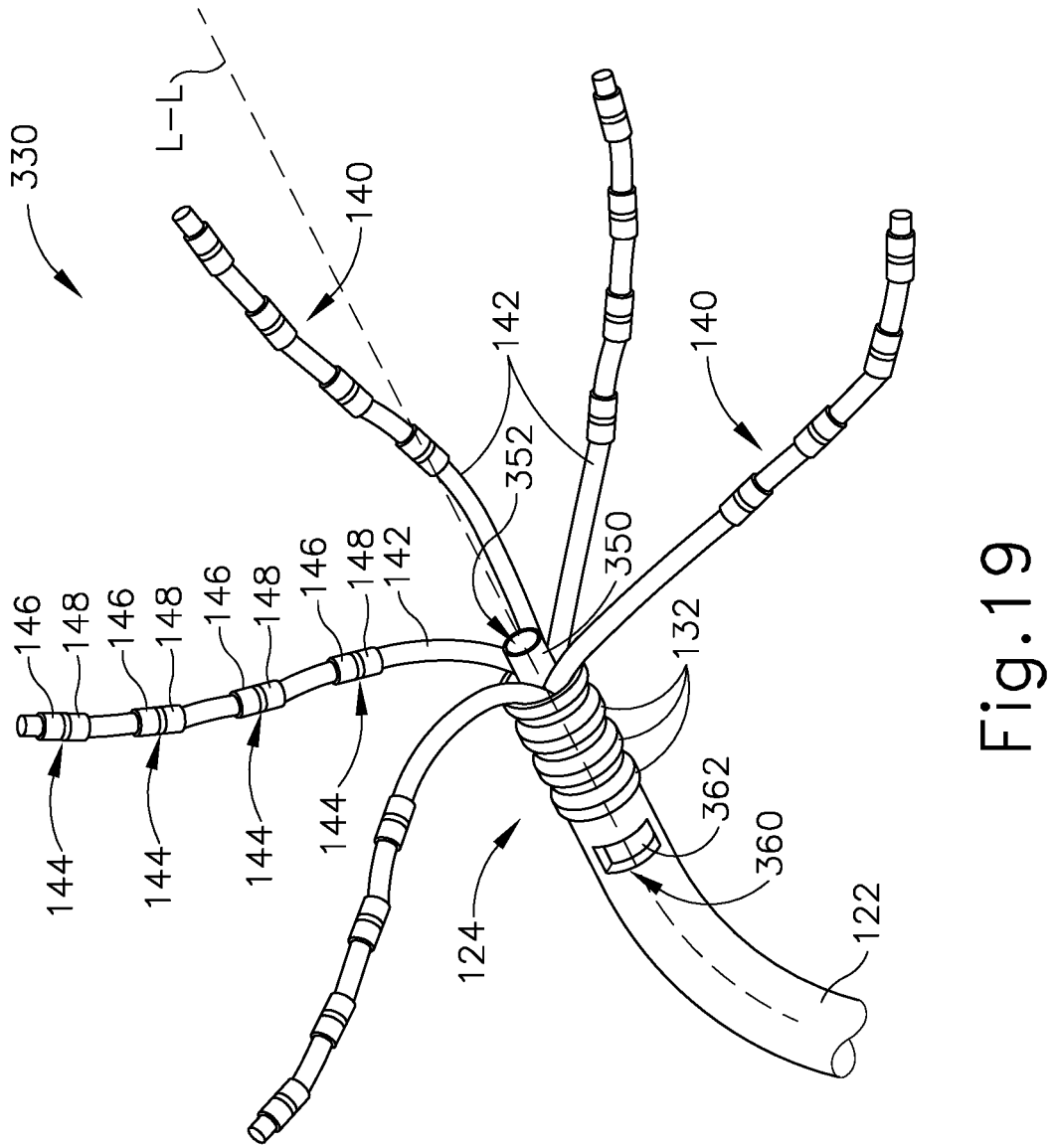
FIG. 19 depicts a perspective view of another exemplary alternative end effector that may be incorporated into the catheter assembly of FIG. 1.

FIG. 19 shows another exemplary end effector (330) that may be incorporated into catheter assembly (100) in place of end effector (130). End effector (330) of this example is configured and operable substantially like end effector (130) described above, such that like components will not be described in further detail here. Like end effector (130), end effector (330) of this example includes a central shaft (350) with a distal opening (352) that is operable to dispense irrigation fluid. However, unlike central shaft (150), central shaft (350) of this example lacks a ring electrode (154). Instead, a reference electrode (362) is positioned on catheter shaft (122) at a location proximal to arms (140) and ring electrodes (132). Reference electrode (362) is positioned in a window (360) formed through catheter shaft (122) such that reference electrode (362) is recessed relative to the outer surface of catheter shaft (122). This recessed positioning may prevent reference electrode (362) from contacting tissue. Blood may nevertheless reach reference electrode (362) via window (360), such that reference electrode (362) may pick up a reference potential from blood that contacts reference electrode (362) via window (360).

During use of end effector (330), one or more electrodes (146, 148) contacting tissue surface (T) may pick up electrical potentials at the contacted regions of the tissue surface (T), while reference electrode (362) picks up a reference potential from the blood contacting reference electrode (362). The processor of console (12) may process the potentials from electrodes (146, 148, 362) and thereby provide an electrocardiogram signal as described above.

By way of further example only, in addition to having the above-described features and functionalities, end effector (330) may be constructed and operable in accordance with at least some of the teachings of U.S. Pub. No. 2016/0374753, entitled "Catheter Having Closed Loop Array with In-Plane Linear Electrode Portion," published Dec. 29, 2016, the disclosure of which is incorporated by reference herein; U.S. Pub. No. 2018/0056038, entitled "Catheter with Bipole Electrode Spacer and Related Methods," published Mar. 1, 2018, the disclosure of which is incorporated by reference herein; U.S. Pat. No. 9,907,480, entitled "Catheter Spine Assembly with Closely-Spaced Bipole Microelectrodes," issued Mar. 6, 2018, the disclosure of which is incorporated by reference herein; U.S. Pat. No. 9,949,656, entitled "Catheter with Stacked Spine Electrode Assembly," issued Apr. 24, 2018, the disclosure of which is incorporated by reference herein; or U.S. Pat. No. 9,820,664, entitled "Catheter with High Density Electrode Spine Array," issued Nov. 21, 2017, the disclosure of which is incorporated by reference herein.

Moreover, any of the other above-described catheter shafts (210, 522, 622, 722, 822, 922, 1022, 1122, 1222, 1322) may incorporate a recessed reference electrode (362) in a manner similar to catheter shaft (122) as described above with reference to FIG. 19. Such a modification may be provided in addition to or in lieu of providing electrode (154, 254, 554, 654, 754, 854, 954, 1054, 1154, 1260, 1360) as described above.

H. Exemplary Multi-Ray End Effector with Covered Proximal Reference Electrode

Figure 20:
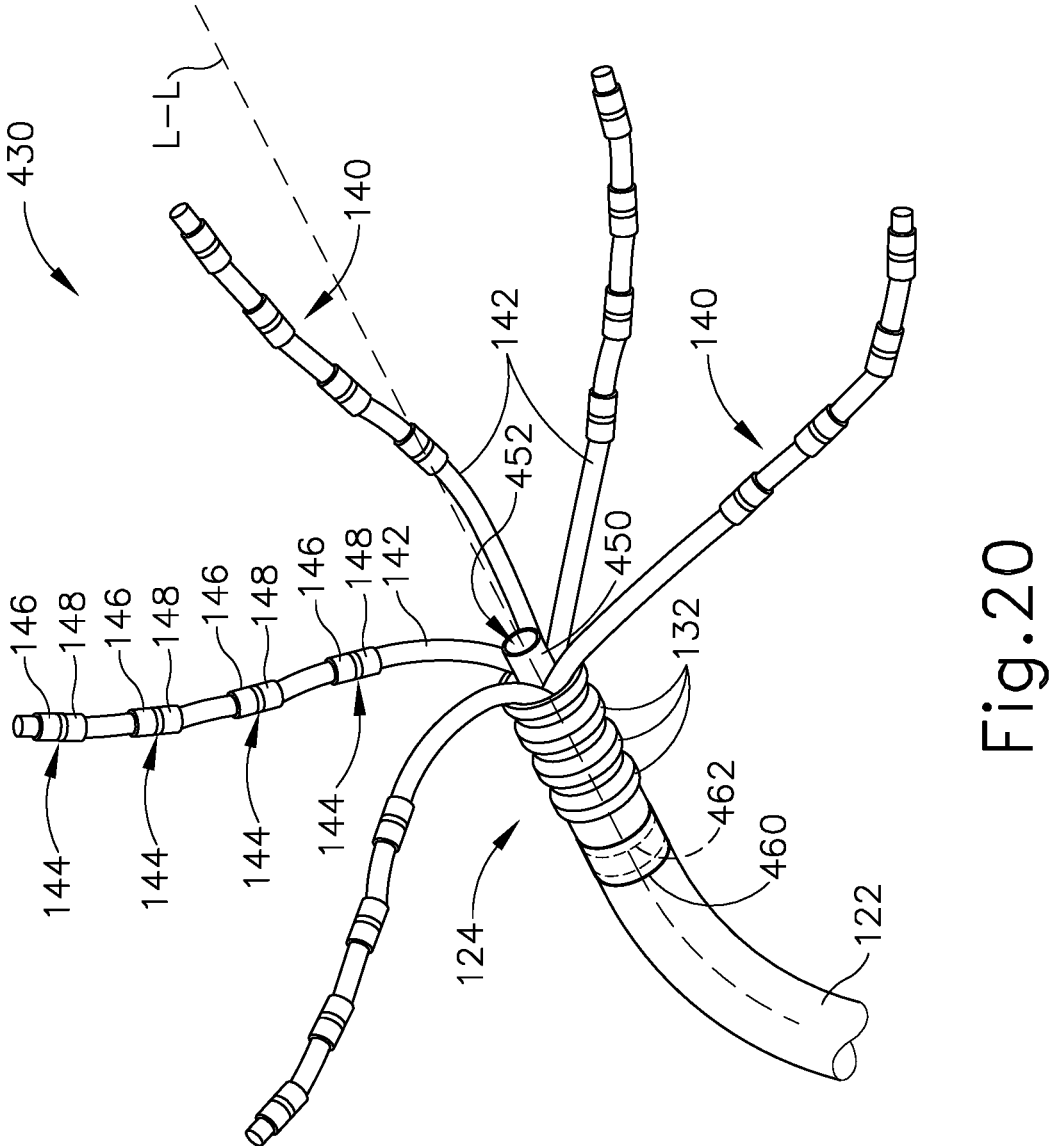
FIG. 20 depicts a perspective view of another exemplary alternative end effector that may be incorporated into the catheter assembly of FIG. 1.

FIG. 20 shows another exemplary end effector (430) that may be incorporated into catheter assembly (100) in place of end effector (130). End effector (430) of this example is configured and operable substantially like end effector (130) described above, such that like components will not be described in further detail here. Like end effector (130), end effector (430) of this example includes a central shaft (450) with a distal opening (452) that is operable to dispense irrigation fluid. However, unlike central shaft (150), central shaft (450) of this example lacks a ring electrode (154). Instead, a reference electrode (462) is positioned on catheter shaft (122) at a location proximal to arms (140) and ring electrodes (132). Reference electrode (462) is positioned underneath a cover-like member or tissue guard (460). Tissue guard (460) fully encompasses reference electrode (462) and is configured to permit blood to contact reference electrode (462) while preventing tissue from contacting reference electrode (462). Tissue guard (460) is not electrically conductive. By way of example only, tissue guard (460) may be formed of a mesh material, a porous structure, a band with several openings formed therein, or any other suitable kind of construction as will be apparent to those skilled in the art in view of the teachings herein. Reference electrode (462) is operable to pick up a reference potential from blood that contacts reference electrode (462) via tissue guard (460).

During use of end effector (430), one or more electrodes (146, 148) contacting tissue surface (T) may pick up electrical potentials at the contacted regions of the tissue surface (T), while reference electrode (462) picks up a reference potential from the blood contacting reference electrode (462). The processor of console (12) may process the potentials from electrodes (146, 148, 462) and thereby provide an electrocardiogram signal as described above.

By way of further example only, in addition to having the above-described features and functionalities, end effector (430) may be constructed and operable in accordance with at least some of the teachings of U.S. Pub. No. 2016/0374753, entitled "Catheter Having Closed Loop Array with In-Plane Linear Electrode Portion," published Dec. 29, 2016, the disclosure of which is incorporated by reference herein; U.S. Pub. No. 2018/0056038, entitled "Catheter with Bipole Electrode Spacer and Related Methods," published Mar. 1, 2018, the disclosure of which is incorporated by reference herein; U.S. Pat. No. 9,907,480, entitled "Catheter Spine Assembly with Closely-Spaced Bipole Microelectrodes," issued Mar. 6, 2018, the disclosure of which is incorporated by reference herein; U.S. Pat. No. 9,949,656, entitled "Catheter with Stacked Spine Electrode Assembly," issued Apr. 24, 2018, the disclosure of which is incorporated by reference herein; or U.S. Pat. No. 9,820,664, entitled "Catheter with High Density Electrode Spine Array," issued Nov. 21, 2017, the disclosure of which is incorporated by reference herein.

Moreover, any of the other above-described catheter shafts (210, 522, 622, 722, 822, 922, 1022, 1122, 1222, 1322) may incorporate a reference electrode (462) with a tissue guard (460) in a manner similar to catheter shaft (122) as described above with reference to FIG. 20. Such a modification may be provided in addition to or in lieu of providing electrode (154, 254, 554, 654, 754, 854, 954, 1054, 1154, 1260, 1360) as described above.

I. Dynamic Assignment of Reference Electrode

Various end effectors (130, 200, 330, 430, 530, 630, 730, 830, 930, 1030, 1130, 1330) described above have electrodes (146, 148, 232, 234, 542, 642, 742, 842, 942, 1042, 1142, 1342) that are configured to contact tissue. During normal use of such end effectors (130, 200, 330, 430, 530, 630, 730, 830, 930, 1030, 1130, 1330), while at least one electrode (146, 148, 232, 234, 542, 642, 742, 842, 942, 1042, 1142, 1342) may be in contact with tissue, at least one other electrode (146, 148, 232, 234, 542, 642, 742, 842, 942, 1042, 1142, 1342) may not be in contact with tissue. Such a non-tissue-contacting electrode (146, 148, 232, 234, 542, 642, 742, 842, 942, 1042, 1142, 1342) may nevertheless be in contact with blood. Such a non-tissue-contacting electrode (146, 148, 232, 234, 542, 642, 742, 842, 942, 1042, 1142, 1342) may thus serve as a reference electrode, just like electrode (154, 254, 554, 654, 754, 854, 954, 1054, 1154, 1260, 1360) described above. In such instances, electrode (154, 254, 554, 654, 754, 854, 954, 1054, 1154, 1260, 1360) may be omitted.

In some scenarios where one electrode (146, 148, 232, 234, 542, 642, 742, 842, 942, 1042, 1142, 1342) serves as a reference electrode, the physician (PH) may observe the signals being picked up by electrode (146, 148, 232, 234, 542, 642, 742, 842, 942, 1042, 1142, 1342) to identify an electrode (146, 148, 232, 234, 542, 642, 742, 842, 942, 1042, 1142, 1342) that is not contacting tissue. Such observations may be made based on signal readouts being rendered via display (18) of guidance and drive system (10). After identifying an electrode (146, 148, 232, 234, 542, 642, 742, 842, 942, 1042, 1142, 1342) that is not contacting tissue, the physician (PH) may flag the non-tissue-contacting electrode (146, 148, 232, 234, 542, 642, 742, 842, 942, 1042, 1142, 1342) as the reference electrode. In some instances, the physician (PH) may also flag a particular tissue-contacting electrode (146, 148, 232, 234, 542, 642, 742, 842, 942, 1042, 1142, 1342) for comparison with the user-identified reference electrode. The processor of console (12) may then process the potentials from the user-identified reference electrode (146, 148, 232, 234, 542, 642, 742, 842, 942, 1042, 1142, 1342) and from a tissue-contacting electrode (146, 148, 232, 234, 542, 642, 742, 842, 942, 1042, 1142, 1342) and thereby provide an electrocardiogram signal as described above.

As an alternative to having the physician (PH) identify the non-tissue-contacting reference electrode (146, 148, 232, 234, 542, 642, 742, 842, 942, 1042, 1142, 1342), the processor of console (12) may automatically identify a non-tissue-contacting electrode (146, 148, 232, 234, 542, 642, 742, 842, 942, 1042, 1142, 1342) and flag that non-tissue-contacting electrode (146, 148, 232, 234, 542, 642, 742, 842, 942, 1042, 1142, 1342) as the reference electrode. By way of example only, processor of console (12) may identify which electrodes (146, 148, 232, 234, 542, 642, 742, 842, 942, 1042, 1142, 1342) are contacting tissue and which electrodes (146, 148, 232, 234, 542, 642, 742, 842, 942, 1042, 1142, 1342) are not contacting tissue based on the impedance at electrodes (146, 148, 232, 234, 542, 642, 742, 842, 942, 1042, 1142, 1342). A non-tissue-contacting electrode (146, 148, 232, 234, 542, 642, 742, 842, 942, 1042,

1142, 1342) may have a lower impedance than a tissue-contacting electrode (146, 148, 232, 234, 542, 642, 742, 842, 942, 1042, 1142, 1342).

As another merely illustrative example, the processor of console (12) may check the impedance between a dedicated reference electrode (154, 254, 554, 654, 754, 854, 954, 1054, 1154, 1260, 1360) and each of the sensor electrodes (146, 148, 232, 234, 542, 642, 742, 842, 942, 1042, 1142, 1342) to identify which sensor electrode(s) (146, 148, 232, 234, 542, 642, 742, 842, 942, 1042, 1142, 1342) is/are contacting tissue and which sensor electrode(s) (146, 148, 232, 234, 542, 642, 742, 842, 942, 1042, 1142, 1342) is/are not contacting tissue. The processor of console (12) may use this information in any suitable fashion as will be apparent to those skilled in the art in view of the teachings herein.

In view of the foregoing, each end effector (130, 200, 330, 430, 530, 630, 730, 830, 930, 1030, 1130, 1330) described herein has at least one tissue-contacting electrode (146, 148, 232, 234, 542, 642, 742, 842, 942, 1042, 1142, 1240, 1342) and at least one non-tissue-contacting electrode (146, 148, 154, 232, 234, 254, 542, 554, 642, 654, 742, 754, 842, 854, 942, 954, 1042, 1054, 1142, 1154, 1260, 1342, 1360). In the case of electrodes (154, 254, 554, 654, 754, 854, 954, 1054, 1154, 1260, 1360), the non-tissue-contacting electrode (154, 254, 554, 654, 754, 854, 954, 1054, 1154, 1260, 1360) may be physically prevented from contacting tissue by other structures of end effector (130, 200, 330, 430, 530, 630, 730, 830, 930, 1030, 1130, 1330). In the case of electrodes (146, 148, 232, 234, 542, 642, 742, 842, 942, 1042, 1142, 1342), the non-tissue-contacting electrode (146, 148, 232, 234, 542, 642, 742, 842, 942, 1042, 1142, 1342) is just incidentally not contacting tissue at a particular stage of the EP mapping procedure.

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a shaft; and (b) an end effector at a distal end of the shaft, the end effector having a distal end and a proximal end with a longitudinal intermediate point between the distal and proximal ends, the end effector being sized to fit in an anatomical passageway within a cardiovascular system, the end effector comprising: (i) at least one sensor electrode, the at least one sensor electrode being configured to contact cardiovascular tissue and thereby pick up potentials, and (ii) a reference electrode configured to pick up a potential from fluid in contact with the reference electrode, the reference electrode being located proximal to the longitudinal intermediate point of the end effector, the end effector being configured to prevent the reference electrode from contacting tissue.

Example 2

The apparatus of Example 1, the end effector defining a profile having a first portion proximal to the longitudinal intermediate point and a second portion proximal to the longitudinal intermediate point, the first portion of the profile being proximal to the second portion of the profile, the profile of the end effector having: (A) a first cross-sectional area at a proximal plane located at the proximal end of the end effector, the proximal plane defining a proximal boundary of the first portion of the profile, (B) a second cross-sectional area at an intermediate plane defining a boundary between the first and second portions of the profile, the second cross-sectional area being substantially equal to the first cross-sectional area, and (C) a third cross-sectional area at a distal plane defining a distal boundary of the second portion of the profile.

Example 3

The apparatus of Example 2, the reference electrode being positioned in the first portion of the profile.

Example 4

The apparatus of Example 2, the first portion of the profile being generally cylindrical.

Example 5

The apparatus of Example 2, the first portion of the profile being generally polygonal.

Example 6

The apparatus of any one or more of Examples 2 through 5, the second profile being generally frusto-conical.

Example 7

The apparatus of Example 6, the second profile being generally bellmouth-shaped.

Example 8

The apparatus of Example 6, the second profile being generally pyramid-shaped.

Example 9

The apparatus of any one or more of Examples 2 through 8, the second profile diverging outwardly from the intermediate plane to the distal plane.

Example 10

The apparatus of any one or more of Examples 1 through 9, the end effector being sized to fit in an anatomical passageway within a human cardiovascular system.

Example 11

The apparatus of any one or more of Examples 1 through 10, the end effector further comprising a plurality of elongated spines and a plurality of the sensor electrodes, the sensor electrodes being secured to the spines.

Example 12

The apparatus of Example 11, the spines being configured to prevent tissue from contacting the reference electrode.

Example 13

The apparatus of any one or more of Examples 11 through 12, the spines being disposed in parallel to each other and connected at a proximal region of the spines to define a generally planar configuration.

Example 14

The apparatus of any one or more of Examples 11 through 12, a first pair of spines being connected at a proximal region to define a first plane and a second pair of spines being connected at a proximal region to define a second plane different from the first plane.

Example 15

The apparatus of any one or more of Examples 11 through 14, the shaft defining a longitudinal axis, a portion of each of the spines extending outwardly away from the longitudinal axis.

Example 16

The apparatus of any one or more of Examples 11 through 15, the shaft defining a longitudinal axis, each of the spines comprising respective free ends oriented away from the longitudinal axis.

Example 17

The apparatus of any one or more of Examples 11 through 16, the shaft defining a longitudinal axis, the end effector further comprising a central shaft extending along the longitudinal axis, the central shaft being shorter than the spines such that the reference electrode is positioned on the central shaft and partially enshrouded by the spines.

Example 18

The apparatus of Example 17, the central shaft of the end effector being further configured to dispense irrigation fluid.

Example 19

The apparatus of any one or more of Examples 11 through 18, the shaft defining a longitudinal axis, the spines being configured to bow outwardly and converge distally with respect to the longitudinal axis to form a basket configuration.

Example 20

The apparatus of Example 19, the reference electrode being positioned in an interior region of the basket configuration.

Example 21

The apparatus of any one or more of Examples 1 through 20, the shaft defining a longitudinal axis, the reference electrode comprising a ring coaxially positioned about the longitudinal axis.

Example 22

The apparatus of any one or more of Examples 1 through 21, the reference electrode being positioned proximally in relation to the at least one sensor electrode.

Example 23

An apparatus, comprising: (a) a shaft extending along a longitudinal axis; and (b) an end effector at a distal end of the shaft, the end effector being sized to fit in an anatomical passageway within a cardiovascular system, the end effector defining a profile oriented with respect to the longitudinal axis that generates about the longitudinal axis a frusto-conical portion and a cylindrical portion proximal to the frusto-conical portion, the end effector comprising: (i) at least one tissue-contacting electrode, the at least one tissue-contacting electrode being configured to contact cardiovascular tissue and thereby pick up potentials, and (ii) a non-tissue contact electrode configured to pick up a reference potential from fluid in contact with the non-tissue contact electrode, the non-tissue contact electrode being positioned in the cylindrical portion of the profile, the end effector being configured to prevent the non-tissue contact electrode from contacting tissue.

Example 24

The apparatus of Example 23 in which the apparatus is capable of being reprocessed into a reusable apparatus for subsequent reuse.

Example 25

The apparatus of Example 24, in which the reprocessed apparatus is cleaned and sterilized with a solution for reuse in a subject.

Example 26

The apparatus of Example 25, in which the solution comprises a chemical selected from a group consisting of: 3300-3800 ppm peracetic acid; 2.65% glutaraldehyde; 3.4% glutaraldehyde with 26% isopropanol; 3.5% glutaraldehyde; 5.75% ortho-phthaldehyde; 0.55% ortho-phthaldehyde; hypochlorite with hypochlorous acid 650-675 ppm active free chlorine; 1.12% glutaraldehyde with 1.93% phenol/phenate; 2.5% glutaraldehyde; 3.2% glutaraldehyde; 3% glutaraldehyde; 7.35% hydrogen peroxide with 0.23% peracetic acid; 1.0% hydrogen peroxide with 0.08% peracetic acid; 2.4% glutaraldehyde; 3.4% glutaraldehyde; 2.0% hydrogen peroxide; 0.60% ortho-phthalaldehyde; hypochlorous acid/hypochlorite 400-450 ppm with active free chlorine; and combinations thereof.

Example 27

A method comprising: (a) placing a first sensor electrode in contact with tissue in a patient's cardiovascular system; (b) positioning a reference electrode in contact with fluid in the patient's cardiovascular system without contact with tissue in the patient's cardiovascular system; (c) processing electrical signals from the first sensor electrode and the reference electrode; (d) plotting an electrocardiogram signal based on the processed electrical signals; and (e) communicating fluid through a lumen, the reference electrode being coaxially positioned about the lumen.

Example 28

The method of Example 27, the step of positioning comprising preventing the reference electrode from contacting tissue with at least one flexible arm that extends away from a longitudinal axis of the reference electrode.

Example 29

The method of any one or more of Examples 27 through 28, the first sensor electrode being positioned on a flexible arm extending outwardly from a central longitudinal axis of a shaft, the reference electrode being positioned about the central longitudinal axis of the shaft.

Example 30

The method of any one or more of Examples 27 through 29, further comprising: (a) placing a second sensor electrode in a patient's cardiovascular system without placing the second sensor electrode in contact with tissue in the patient's cardiovascular system; (b) measuring impedance between the reference electrode and the first sensor electrode; (c) measuring impedance between the reference electrode and the second sensor electrode; and (d) determining that the first sensor electrode is in contact with tissue and that the second sensor electrode is not in contact with tissue based on the measured impedances.

Example 31

The method of Example 30, the measured impedance between the reference electrode and the first sensor electrode being greater than the measured impedance between the reference electrode and the second sensor electrode, the step of determining that the first sensor electrode is in contact with tissue and that the second sensor electrode is not in contact with tissue comprising determining that the measured impedance between the reference electrode and the first sensor electrode is greater than the measured impedance between the reference electrode and the second sensor electrode.

Example 32

The method of any one or more of Examples 27 through 31, the step of plotting comprising displaying unipolar signal waveform with reduction of far field signals in a range from 50% to 100% compared to Wilson Central Terminal (WCT) reference signals.

Example 33

An apparatus, comprising: (a) a shaft; and (b) a tip member positioned at a distal end of the shaft, the tip member defining a hollow interior and an opening in fluid communication with the hollow interior; (c) at least a pair of spines extending from the distal end of the shaft along a longitudinal axis to define a virtual volume about the tip member; and (d) a non-tissue contact electrode positioned proximate the opening of the tip member, the non-tissue contact electrode being configured to pick up a reference potential and the tip member being configured to prevent the non-tissue contact electrode from contacting tissue.

Example 34

The apparatus of Example 33, in which the non-tissue contact electrode is disposed inside the hollow interior.

Example 35

The apparatus of Example 33, in which the non-tissue contact electrode is disposed outside of the hollow interior.

Example 36

An apparatus, comprising: (a) a shaft including an outer surface defining a lateral window; and (b) an end effector at a distal end of the shaft, the end effector being sized to fit in an anatomical passageway within a cardiovascular system, the end effector comprising: (i) at least one sensor electrode, the at least one sensor electrode being configured to contact cardiovascular tissue and thereby pick up potentials, and (ii) a reference electrode configured to pick up a potential from fluid in contact with the electrode, the reference electrode being accessible via the lateral window, the shaft being configured to prevent tissue from contacting the reference electrode.

Example 37

The apparatus of Example 36, the reference electrode being recessed relative to the outer surface of the shaft.

Example 38

An apparatus, comprising: (a) a shaft; (b) an end effector at a distal end of the shaft, the end effector being sized to fit in an anatomical passageway within a cardiovascular system, the end effector comprising at least one sensor electrode, the at least one sensor electrode being configured to contact cardiovascular tissue and thereby pick up potentials; (c) an electrode cover member disposed on the shaft; and (d) a reference electrode configured to pick up a potential from fluid in contact with the reference electrode, the reference electrode being positioned underneath the electrode cover member, the electrode cover member being configured to allow blood to contact the reference electrode while preventing tissue from contacting the reference electrode.

Example 39

The apparatus of Example 38, the electrode cover member being porous.

Example 40

The apparatus of any one or more of Examples 38 through 39, the shaft defining a longitudinal axis, the electrode cover member being coaxially positioned about the longitudinal axis.

III. Miscellaneous

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

By way of example only, when one of the instruments described herein is cleaned and sterilized before and/or after a procedure such cleaning and reprocessing may be carried out using a solution. By way of further example only, such a solution may comprise a chemical selected from a group consisting of: 3300-3800 ppm peracetic acid; 2.65% glutaraldehyde; 3.4% glutaraldehyde with 26% isopropanol; 3.5% glutaraldehyde; 5.75% ortho-phthaldehyde; 0.55% ortho-phthaldehyde; hypochlorite with hypochlorous acid 650-675 ppm active free chlorine; 1.12% glutaraldehyde with 1.93% phenol/phenate; 2.5% glutaraldehyde; 3.2% glutaraldehyde; 3% glutaraldehyde; 7.35% hydrogen peroxide with 0.23% peracetic acid; 1.0% hydrogen peroxide with 0.08% peracetic acid; 2.4% glutaraldehyde; 3.4% glutaraldehyde; 2.0% hydrogen peroxide; 0.60% ortho-phthalaldehyde; hypochlorous acid/hypochlorite 400-450 ppm with active free chlorine; and combinations thereof. As another merely illustrative example, such a solution may comprise a chemical selected from a group consisting of: 3100-3400 ppm peracetic acid; 3.4% glutaraldehyde with 20.1% isopropanol; 2.0% hydrogen peroxide; at least 1820 mg/L peracetic acid; 0.575% ortho-phthalaldehyde; 0.60% ortho-phthalaldehyde; hypochlorite and hypochlorous acid with 650-675 ppm active free chlorine; 0.55% ortho-phthalaldehyde; 7.5% hydrogen peroxide; 2.6% glutaraldehyde; hypochlorite and hypochlorous acid with 400-450 ppm active free chlorine; 0.55% ortho-phthalaldehyde; and combinations thereof. The cleaning and/or sterilization procedures may be carried out in accordance with the U.S. Food & Drug Administration guidelines as published at https://www.fda-.gov/medical-devices/reprocessing-reusable-medical-devices-information-manufacturers/fda-cleared-sterilants-and-high-level-disinfectants-general-claims-processing-reusable-medical-and, the disclosure of which is incorporated by reference herein in its entirety.

By way of example only, when one of the instruments described herein is cleaned and sterilized before and/or after a procedure such cleaning and reprocessing may be carried out using a sterilization system such as those described in U.S. Pat. No. 6,939,519, entitled "Power System for Sterilization Systems Employing Low Frequency Plasma," issued Sep. 6, 2005, the disclosure of which is incorporated by reference herein in its entirety; U.S. Pat. No. 6,852,279, entitled "Sterilization with Temperature-Controlled Diffusion Path," issued Feb. 8, 2005, the disclosure of which is incorporated by reference herein in its entirety; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein in its entirety; U.S. Pat. No. 6,447,719, entitled "Power System for Sterilization Systems Employing Low Frequency Plasma," issued Sep. 10, 2002, the disclosure of which is incorporated by reference herein in its entirety; and U.S. Pub. No. 2017/0252474, entitled "Method of Sterilizing Medical Devices, Analyzing Biological Indicators, and Linking Medical Device Sterilization Equipment" published Sep. 7, 2017, the disclosure of which is incorporated by reference herein in its entirety. Some sterilization systems may use vaporized chemical sterilants or chemical gas such as hydrogen peroxide, peracetic acid, ozone, chlorine dioxide, nitrogen dioxide, etc., to sterilize medical devices. Examples of such systems are described in U.S. Pat. No. 6,365,102, entitled "Method of Enhanced Sterilization with Improved Material Compatibility," issued Apr. 2, 2002, the disclosure of which is incorporated by reference herein in its entirety; and U.S. Pat. No. 6,325,972, entitled "Apparatus and Process for Concentrating a Liquid Sterilant and Sterilizing Articles Therewith," issued Dec. 4, 2001, the disclosure of which is incorporated by reference herein in its entirety.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
(a) a shaft; and
(b) an end effector at a distal end of the shaft, the end effector having a distal end and a proximal end with a longitudinal midpoint between the distal and proximal ends of the end effector, the end effector being sized to fit in an anatomical passageway within a cardiovascular system, the end effector comprising:
(i) a plurality of elongated spines having proximal ends at the distal end of the shaft, the plurality of elongated spines extending distally from the distal end of the shaft, each spine carrying at least one sensor electrode, the at least one sensor electrode being configured to contact cardiovascular tissue and thereby pick up potentials, and
(ii) a central end effector shaft that is shorter than the plurality of spines and fixedly connected to the distal end of the shaft, the central end effector shaft having a proximal portion extending distally from the distal end of the shaft and a distal portion terminating in a distal end that is proximal to the longitudinal midpoint of the end effector and near the proximal ends of the plurality of elongated spines, the proximal portion of the central end effector shaft carrying a circumferential reference electrode spaced from the distal end of the distal portion and configured to pick up a potential from fluid in contact with the reference electrode,
the plurality of spines and the central end effector shaft being configured to prevent the reference electrode from contacting tissue such that any tissue contact with the central end effector shaft occurs at the distal end of the distal portion of the central end effector shaft thereby shielding the circumferential reference electrode from contact with the tissue.
2. The apparatus of claim 1, the end effector defining a profile having a first portion proximal to the longitudinal midpoint and a second portion proximal to the longitudinal midpoint, the first portion of the profile being proximal to the second portion of the profile, the profile of the end effector having:
(A) a first cross-sectional area at a proximal plane located at the proximal end of the end effector, the proximal plane defining a proximal boundary of the first portion of the profile,
(B) a second cross-sectional area at an intermediate plane defining a boundary between the first and second portions of the profile, the second cross-sectional area being substantially equal to the first cross-sectional area, and
(C) a third cross-sectional area at a distal plane defining a distal boundary of the second portion of the profile.
3. The apparatus of claim 2, the reference electrode being positioned in the first portion of the profile.
4. The apparatus of claim 2, the first portion of the profile being generally cylindrical.
5. The apparatus of claim 2, the first portion of the profile being generally polygonal.
6. The apparatus of claim 2, the second portion of the profile being generally frusto-conical.
7. The apparatus of claim 6, the second portion of the profile being generally bellmouth-shaped.
8. The apparatus of claim 6, the second portion of the profile being generally pyramid-shaped.
9. The apparatus of claim 2, the second portion of the profile diverging outwardly from the intermediate plane to the distal plane.
10. The apparatus of claim 1, the at least one sensor electrode comprising a plurality of sensor electrodes carried on each of the plurality of spines.

11. The apparatus of claim 1, the spines of the plurality of spines being disposed in parallel to each other and connected at a proximal region of the spines to define a generally planar configuration.

12. The apparatus of claim 1, a first pair of spines of the plurality of spines being connected at a first proximal region to define a first plane and a second pair of spines of the plurality of spines being connected at a second proximal region to define a second plane different from the first plane.

13. The apparatus of claim 1, the shaft defining a longitudinal axis, a portion of each of the plurality of spines extending outwardly away from the longitudinal axis.

14. The apparatus of claim 1, the shaft defining a longitudinal axis, each of the plurality of spines comprising respective free ends oriented away from the longitudinal axis.

15. The apparatus of claim 1, the shaft defining a longitudinal axis, the central end effector shaft extending from the distal end of the shaft along the longitudinal axis of the shaft such that the reference electrode is positioned on the central end effector shaft and partially enshrouded by the spines.

16. The apparatus of claim 1, the central end effector shaft being further configured to dispense irrigation fluid.

17. The apparatus of claim 1, the shaft defining a longitudinal axis, the plurality of spines being configured to bow outwardly and converge distally with respect to the longitudinal axis to form a basket configuration.

18. The apparatus of claim 17, the central end effector shaft carrying the reference electrode such that it is positioned in an interior region of the basket configuration.

19. The apparatus of claim 1, the reference electrode being positioned proximally in relation to the at least one sensor electrode.

20. The apparatus of claim 1, the plurality of spines and the central end effector shaft being configured to prevent the central end effector shaft from contacting tissue when the plurality of spines are generally flattened on the tissue.

21. The apparatus of claim 1, the plurality of spines and the central end effector shaft being configured to prevent the reference electrode from contacting tissue when the plurality of spines are generally flattened on the tissue such that any tissue contact with the central end effector shaft occurs at the distal end of the distal portion of the central end effector shaft thereby shielding the reference electrode from contact with the tissue.

22. The apparatus of claim 14, the plurality of spines and the central end effector shaft being configured to prevent the central end effector shaft from contacting tissue when the plurality of spines are generally flattened on the tissue.

23. The apparatus of claim 14, the plurality of spines and the central end effector shaft being configured to prevent the reference electrode from contacting tissue when the plurality of spines are generally flattened on the tissue such that any tissue contact with the central end effector shaft occurs at the distal end of the distal portion of the central end effector shaft thereby shielding the reference electrode from contact with the tissue.

24. An apparatus, comprising:
(a) a shaft extending along a longitudinal axis; and
(b) an end effector at a distal end of the shaft, the end effector being sized to fit in an anatomical passageway within a cardiovascular system, the end effector defining a profile oriented with respect to the longitudinal axis that generates about the longitudinal axis a frusto-conical portion and a cylindrical portion proximal to the frusto-conical portion, the end effector comprising:

(i) at least one tissue-contacting electrode, the at least one tissue-contacting electrode being configured to contact cardiovascular tissue and thereby pick up potentials,
(ii) a non-tissue contact electrode configured to pick up a reference potential from fluid in contact with the non-tissue contact electrode, the non-tissue contact electrode being positioned in the cylindrical portion of the profile,
(iii) a plurality of elongated spines having proximal ends at the distal end of the shaft, the plurality of elongated spines extending distally from the distal end of the shaft, the at least one tissue-contacting electrode being carried on at least one of the plurality of elongated spines, and
(iv) a central end effector shaft that is shorter than the plurality of elongated spines and fixedly connected to the distal end of the shaft, the central end effector shaft having a proximal portion extending distally from the distal end of the shaft and a distal portion terminating in a distal end that is proximal to a longitudinal midpoint of the end effector and near the proximal ends of the plurality of elongated spines, the proximal portion of the central end effector shaft carrying the non-tissue contact electrode spaced from the distal end of the distal portion,
the end effector being configured to prevent the non-tissue contact electrode from contacting tissue such that any tissue contact with the central end effector shaft occurs at the distal end of the distal portion of the central end effector shaft thereby shielding the non-tissue contact electrode from contact with the tissue.

25. The apparatus of claim 24, in which the apparatus is capable of being reprocessed into a reusable apparatus for subsequent reuse.

26. The apparatus of claim 25, in which the reprocessed apparatus is cleaned and sterilized with a solution for reuse in a subject.

27. The apparatus of claim 26, in which the solution comprises a chemical selected from the group consisting of: 3300-3800 ppm peracetic acid; 2.65% glutaraldehyde; 3.4% glutaraldehyde with 26% isopropanol; 3.5% glutaraldehyde; 5.75% ortho-phthaldehyde; 0.55% ortho-phthaldehyde; hypochlorite with hypochlorous acid 650-675 ppm active free chlorine; 1.12% glutaraldehyde with 1.93% phenol/phenate; 2.5% glutaraldehyde; 3.2% glutaraldehyde; 3% glutaraldehyde; 7.35% hydrogen peroxide with 0.23% peracetic acid; 1.0% hydrogen peroxide with 0.08% peracetic acid; 2.4% glutaraldehyde; 3.4% glutaraldehyde; 2.0% hydrogen peroxide; 0.60% ortho-phthalaldehyde; hypochlorous acid/hypochlorite 400-450 ppm with active free chlorine; and combinations thereof.

28. The apparatus of claim 24, the end effector being configured to prevent the central end effector shaft from contacting tissue when the plurality of spines are generally flattened on the tissue.

29. The apparatus of claim 24, the end effector being configured to prevent the non-tissue contact electrode from contacting tissue when the plurality of spines are generally flattened on the tissue such that any tissue contact with the central end effector shaft occurs at the distal end of the distal portion of the central end effector shaft thereby shielding the non-tissue contact electrode from contact with the tissue.

30. An apparatus, comprising:
(a) a shaft; and
(b) a tip shaft fixedly connected to a distal end of the shaft and having a proximal portion extending distally from a distal end of the shaft and a distal portion terminating in a distal end, the tip shaft defining a hollow interior and a distal opening in fluid communication with the hollow interior;

(c) a plurality of spines having proximal ends at the distal end of the shaft, the plurality of spines extending distally from the distal end of the shaft along a longitudinal axis to define a virtual volume about the tip shaft, the plurality of spines being longer than the tip shaft such that the distal end of the distal portion of the tip shaft is proximal of a longitudinal midpoint between the distal end of the shaft and distal ends of the plurality of spines and near the proximal ends of the plurality of spines; and (d) a circumferential non-tissue contact electrode carried by the proximal portion of the tip shaft at a position spaced proximally from the distal opening at the distal end of the distal portion of the tip shaft, the non-tissue contact electrode being configured to pick up a reference potential, and the plurality of spines and the tip shaft being configured to prevent the non-tissue contact electrode from contacting tissue such that any tissue contact with the tip shaft occurs at the distal end of the distal portion of the tip shaft thereby shielding the circumferential non-tissue contact electrode from contact with the tissue.

31. The apparatus of claim 30, in which the circumferential non-tissue contact electrode is disposed on an inner circumferential surface of the hollow interior of the tip shaft.

32. The apparatus of claim 30, in which the circumferential non-tissue contact electrode is disposed on an outer circumferential surface of the tip shaft.

33. The apparatus of claim 30, the plurality of spines and the tip shaft being configured to prevent the tip shaft from contacting tissue when the plurality of spines are generally flattened on the tissue.

34. The apparatus of claim 30, the plurality of spines and the tip shaft being configured to prevent the non-tissue contact electrode from contacting tissue when the plurality of spines are generally flattened on the tissue such that any tissue contact with the tip shaft occurs at the distal end of the distal portion of the tip shaft thereby shielding the non-tissue contact electrode from contact with the tissue.

35. A method of using the apparatus of claim 1, the method comprising:
(a) placing a first sensor electrode of the at least one sensor electrode in contact with tissue in a patient's cardiovascular system;
(b) positioning the reference electrode in contact with fluid in the patient's cardiovascular system without contact with tissue in the patient's cardiovascular system;
(c) processing electrical signals from the first sensor electrode and the reference electrode;
(d) plotting an electrocardiogram signal based on the processed electrical signals;
(e) communicating fluid through a lumen of the central end effector shaft, the reference electrode being coaxially positioned about the lumen.

36. The method of claim 35, the at least one sensor electrode comprising the first sensor electrode and a second sensor electrode, the method further comprising:
(a) placing the second sensor electrode in the patient's cardiovascular system without placing the second sensor electrode in contact with tissue in the patient's cardiovascular system;
(b) measuring impedance between the reference electrode and the first sensor electrode;
(c) measuring impedance between the reference electrode and the second sensor electrode; and
(d) determining that the first sensor electrode is in contact with tissue and that the second sensor electrode is not in contact with tissue based on the measured impedances.

37. The method of claim 36, the measured impedance between the reference electrode and the first sensor electrode being greater than the measured impedance between the reference electrode and the second sensor electrode, the step of determining that the first sensor electrode is in contact with tissue and that the second sensor electrode is not in contact with tissue comprising determining that the measured impedance between the reference electrode and the first sensor electrode is greater than the measured impedance between the reference electrode and the second sensor electrode.

38. The method of claim 35, the step of plotting comprising displaying a unipolar signal waveform with reduction of far field signals in a range from 50% to 100% compared to Wilson Central Terminal (WCT) reference signals.

* * * * *